United States Patent [19]

Mori et al.

[11] Patent Number: 5,118,441
[45] Date of Patent: Jun. 2, 1992

[54] MESOMORPHIC COMPOUND, LIQUID CRYSTAL COMPOSITION AND LIQUID CRYSTAL DEVICE USING SAME

[75] Inventors: Shosei Mori, Atsugi; Takeshi Togano, Yokohama; Takao Takiguchi, Tokyo; Takashi Iwaki, Isehara; Yoko Yamada, Atsugi, all of Japan

[73] Assignee: Canon Kabushiki Kaisha, Tokyo, Japan

[21] Appl. No.: 507,480

[22] Filed: Apr. 11, 1990

[30] Foreign Application Priority Data

Apr. 14, 1989 [JP] Japan ................................. 1-95018

[51] Int. Cl.$^5$ .................... C09K 19/34; C07D 331/02; C07D 333/02
[52] U.S. Cl. .................. 252/299.61; 549/1; 549/29
[58] Field of Search ................... 252/299.61; 549/1, 29

[56] References Cited

U.S. PATENT DOCUMENTS

| | | | |
|---|---|---|---|
| 4,367,924 | 1/1983 | Clark et al. | 350/334 |
| 4,639,328 | 1/1987 | Krause et al. | 252/299.61 |
| 4,902,107 | 2/1990 | Tsuboyama et al. | 350/350 S |
| 4,904,410 | 2/1990 | Nohira et al. | 252/299.61 |
| 4,918,213 | 4/1990 | Nohira et al. | 558/271 |

FOREIGN PATENT DOCUMENTS

| | | |
|---|---|---|
| 2518999 | 7/1983 | France . |
| 107216 | 8/1981 | Japan . |
| 193426 | 11/1984 | Japan . |
| 193427 | 11/1984 | Japan . |
| 156046 | 8/1985 | Japan . |
| 156047 | 8/1985 | Japan . |
| 245142 | 10/1986 | Japan . |
| 246722 | 10/1986 | Japan . |
| 246723 | 10/1986 | Japan . |
| 246724 | 10/1986 | Japan . |
| 249024 | 11/1986 | Japan . |
| 249025 | 11/1986 | Japan . |
| 2022778 | 1/1987 | Japan . |
| WO04874 | 11/1985 | PCT Int'l Appl. . |

OTHER PUBLICATIONS

Appl. Phys. Lett., vol. 18, No. 4 (Feb. 1971).
Die Praxis des Organischen Chemikers (1925) 212:217.
Journal of the American Chemical Society, vol. 63 (1941) 196.
Journal of the American Chemical Society, vol. 79 (1957) 427.
Chemical and Pharmaceutical Bulletin, vol. 18, No. 3 (Mar. 1970) 587:590.

*Primary Examiner*—Robert L. Stoll
*Assistant Examiner*—C. Harris
*Attorney, Agent, or Firm*—Fitzpatrick Cella, Harper & Scinto

[57] ABSTRACT

A mesomorphic compound represented by the following formula (I):

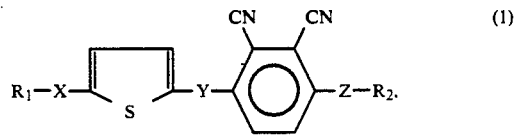

wherein $R_1$ and $R_2$ respectively denote a linear or branched alkyl group having 1-18 carbon atoms capable of having a substituent; X denotes any one of a single bond, —O—,

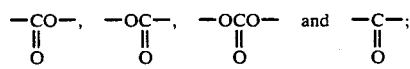

Y denotes

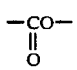

or —CH$_2$O—; and Z denotes any one of —O—, 47 Claims, 3 Drawing Sheets

MESOMORPHIC COMPOUND, LIQUID CRYSTAL COMPOSITION AND LIQUID CRYSTAL DEVICE USING SAME

FIELD OF THE INVENTION AND RELATED ART

The present invention relates to a novel mesomorphic compound, a ferroelectric liquid crystal composition containing the compound and a ferroelectric liquid crystal device using the composition.

Clark and Lagerwall proposed a ferroelectric liquid crystal display system, called an SSFLC (Surface Stabilized Ferroelectric Liquid Crystal) System in 1980. The SSFLC system is principally characterized in release of a helical structure (having a pitch of $l_0$) owned by a ferroelectric liquid crystal (hereinafter sometimes abbreviated as "FLC") by utilizing the boundary effect of a pair of substrate surfaces, more specifically through the following features.

(1) The spacing (cell gap) between the pair of substrates is set to a sufficiently small value to release the above-mentioned helical structure.

(2) The liquid crystal molecules are set to align in parallel with the boundaries with the substrates, whereby the smectic layers of FLC are disposed perpendicularly to the substrates.

(3) Further, the direction of the alignment of liquid crystal molecules in contact with at least one of the substrates is regulated, whereby the direction of the smectic layers is uniformized over the entire cell area.

When the alignment state formed through such stepwise molecular control is viewed macroscopically, stable longer-axis directions (director ñ) of ferroelectric liquid crystal molecules are restricted to two directions. In an FLC display, the fact that the two directions (average directions of ñ) are discriminateable by means of a polarizer is utilized for display.

The basic mechanism of switching between the above-mentioned two stable directions is based on the utilization of a ferroelectricity which FLC shows in its smectic C* phase. FLC has a molecular dipole moment ($\vec{\mu}$) in a plane parallel to the smectic layer and is present between the cell substrates in such a form that it is disposed continuously while changing the direction of the dipole moment ($\vec{\mu}$) to some extent to provide an average spontaneous polarization (Ps) in a direction from the lower substrate to the upper substrate or in the reverse direction. Each of the directions (upward and downward) of the spontaneous polarization (Ps) corresponds to either one of the above-mentioned molecular longer axes (ñ), so that switching by electric fields becomes possible.

More specifically, when an electric field is applied to the FLC layer from outside, the dipole moments ($\mu$) in the layer are all uniformly oriented (U1) in the direction of the electric field, and when the electric field is removed, the dipole moments are settled at a state (S1) after some relaxation time (on the order of 1 $\mu$s–2 ms varying depending on an FLC used). U1 is a uniform state having a higher degree of order and optically a better uniaxial characteristic than S1, and S1 is a twisted state where the dipoles of FLC are somewhat twisted to provide a lower uniaxial characteristic than U1 but the directions of the spontaneous polarizations are uniform. Similarly, when the polarity of the external electric field is reversed, there are formed states U2 and S2. As a result, it is possible to select U1 or U2 (and thus S1 or S2) by the polarity of the electric field applied.

In a representative FLC cell structure, a pair of substrates are disposed, each substrate of e.g. glass being provided with an electrode pattern of e.g. ITO, further thereon with a layer of e.g. $SiO_2$ (about 1000 Å) for preventing short circuit between the pair of substrates and further thereon with a film of e.g. polyimide (PI; such as SP-510, 710, . . . available from Toray K.K.) of about 400 Å in thickness, which is then treated for alignment control by rubbing with e.g. an acetate fiber-planted cloth. Such a pair of substrates are disposed opposite to each other so that their alignment control directions are symmetrical and the spacing between the substrates is held at 1–3 microns.

On the other hand, it is known that the FLC molecules aligned under such conditions are disposed in succession so that their directors ñ are twisted between the substrates and do not show a uniaxial alignment or orientation (S1, S2 mentioned above). A problem in this case is a low transmittance through the liquid crystal layer.

The optical selection between the two stable states is effected by disposing a pair of polarizers in cross nicols between which the above cell is interposed, and when the absorption axis of the polarizers is disposed in alignment with the average molecular axis of either one of S1 and S2, e.g. S1, the resultant transmittance becomes extremely low to display "black". Then, when the molecular position is switched to the S2 state, the molecular position is deviated from the absorption axis of the polarizers by $2\theta a$ which is an angle between S1 and S2, so that transmission of light is caused to display "white".

The transmitted light intensity I is given by the following equation with respect to the incident light intensity $I_0$ under cross nicols when the uniaxial alignment of the molecules is assumed:

$$I = I_0 \sin^2(4\theta a) \cdot \sin^2(\pi \Delta n d / \lambda) \quad (1),$$

wherein $\Delta n$ denotes the refractive index anisotropy of the FLC; d, the cell thickness; and $\lambda$, the wavelength of the incident light.

When the above-mentioned cell is used, it has been experimentally known that $\theta a$ is 5–8 degrees under a twisted alignment condition and is little affected by a liquid crystal material used.

The control of physical properties affecting the term $\Delta n d \pi / \lambda$ cannot be easily performed, so that it is desired to increase $\theta a$ to increase I. However, this has not been successfully accomplished by only a static alignment technique.

With respect to such a problem, it has been proposed to utilize a torque relating to a dielectric anisotropy $\Delta \epsilon$ of an FLC (1983 SID report from AT & T; Japanese Laid-Open Patent Applns. 245142/1986, 246722/1986, 246723/1986, 246724/1986, 249024/1986 and 249025/1986). More specifically, an effective value of AC electric field is applied in a period other than switching so that the molecular stable states are shifted from S1 and S2 under the electric field due to the generation of a dielectric polarization (AC stabilization effect). A torque $\rho$Ps acting on FLC molecules involved in switching of states and a torque $\rho \Delta \epsilon$ acting on FLC molecules relating to the AC stabilization effect are respectively proportional to physical properties as shown in the following formulas:

$$pPs \, \alpha Ps \, E \quad (2),$$

$$p\Delta\epsilon \alpha \frac{1}{2}\Delta\epsilon \cdot \epsilon_0 \cdot E^2 \quad (3),$$

wherein E is an applied voltage and $\epsilon_0$ is electric constant. The above formula (3) apparently shows that the sign and absolute value of $\Delta\epsilon$ of the FLC play an important role.

FIG. 4 attached hereto shows the change of $\theta a$ versus Vrms experimentally measured for 4 FLC's having different values of $\Delta\epsilon$. The measurement was conducted under application of AC rectangular pulses of 60 KHz so as to remove the influence of Ps. The curves (I)–(IV) correspond to the results obtained by using FLC's showing the following $\Delta\epsilon$ values:

(I) $\Delta\epsilon \approx 5.5$, (II) $\Delta\epsilon \approx 3.0$,
(III) $\Delta\epsilon \approx 0$, (IV) $\Delta\epsilon \approx 1.0$.

Qualitatively, the order of $\Delta\epsilon$ was (I)<(II)<(III)<(IV).

As is clear from the graph in the figure, a larger negative value of $\Delta\epsilon$ provides a large $\theta a$ at a lower voltage and thus contributes to provision of an increased I.

The transmittances obtained by using the liquid crystals (I) and (III) were 15% for (I) and 6% for (III), thus showing a clear difference.

As is known from the above examples, the display characteristics of an SSFLC can be remarkably changed by controlling the properties relating to $\Delta\epsilon$ and Ps.

However, most of ferroelectric liquid crystal compositions used heretofore have a $\Delta\epsilon$ of nearly 0, so that an improvement in display characteristics through the above-mentioned AC stabilization effect can hardly be expected.

On the other hand, liquid crystal compositions having negatively large $\Delta\epsilon$ and comprising at least one species of mesomorphic compound having negative $\Delta\epsilon$ used heretofore have drawbacks of poor response characteristics.

SUMMARY OF THE INVENTION

An object in general of the present invention is to solve the above-mentioned problems.

A specific object of the present invention is to provide a liquid crystal composition and a liquid crystal device using the composition showing excellent response characteristics and providing an AC stabilization effect through utilization of a novel mesomorphic compound having a negative $\Delta\epsilon$.

According to the present invention, there is provided a mesomorphic compound represented by the following formula (I):

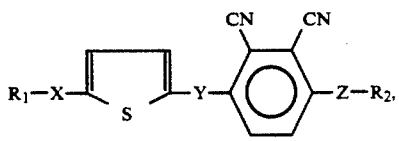

(I)

wherein $R_1$ and $R_2$ respectively denote a linear or branched alkyl group having 1-18 carbon atoms capable of having a substituent; X denotes any one of a single bond, —O—, $$-\underset{\underset{O}{\|}}{C}O-, \quad -O\underset{\underset{O}{\|}}{C}-, \quad -O\underset{\underset{O}{\|}}{C}O- \quad \text{and} \quad -\underset{\underset{O}{\|}}{C}-;$$

Y denotes $$-\underset{\underset{O}{\|}}{C}O-$$

or —CH$_2$O—; and Z denotes any one of —O—, $$-O\underset{\underset{O}{\|}}{C}- \quad \text{and} \quad -O\underset{\underset{O}{\|}}{C}O-.$$

The present invention further provides a ferroelectric chiral smectic liquid crystal composition comprising at least one species of the mesomorphic compound, as described above, and a ferroelectric liquid crystal device comprising such a ferroelectric liquid crystal composition disposed between a pair of substrates.

These and other objects, features and advantages of the present invention will become more apparent upon a consideration of the following description of the preferred embodiments of the present invention taken in conjunction with the accompanying drawings.

DETAILED DESCRIPTION OF THE INVENTION

Figure 1:
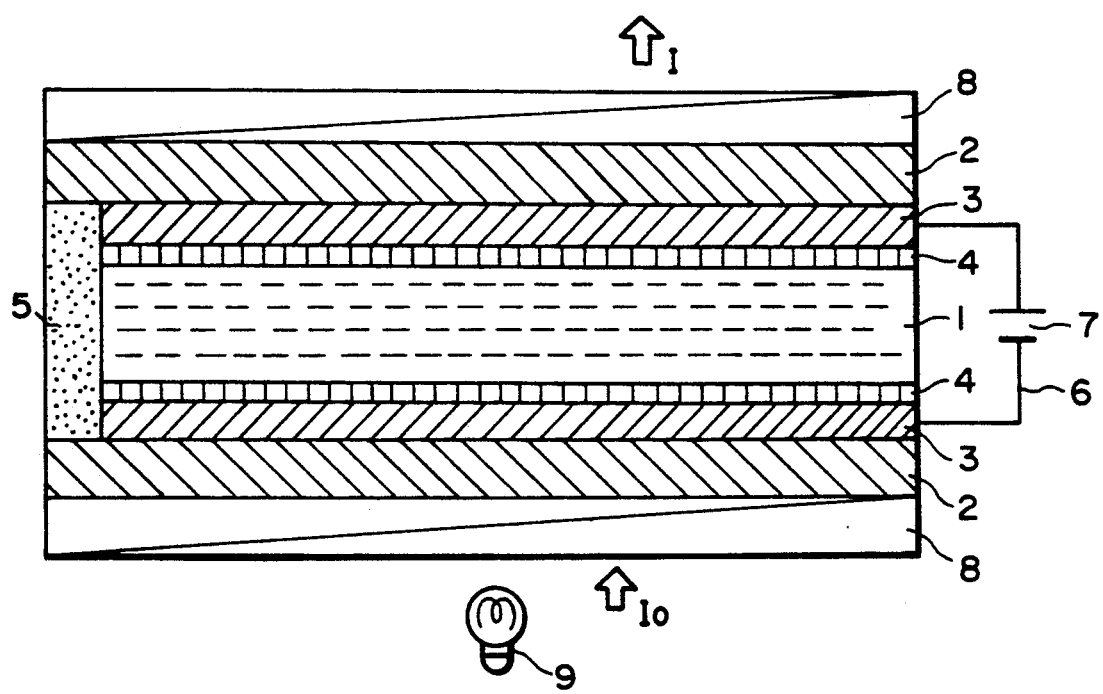
FIG. 1 is a schematic sectional view of a liquid crystal display device using a ferroelectric liquid crystal.

In the formula (I) as described above, preferred examples of X may include a single bond, —O— and $$-\underset{\underset{O}{\|}}{C}-.$$

Further, preferred examples of $R_1$ and $R_2$ in the formula (I) may include the following groups (i) to (iv):

(i) n-alkyl group having 1-18 carbon atoms;

(ii)

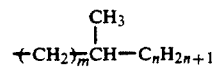

wherein m is 1-7 an n is 2-9 (optically active or inactive);

(iii)

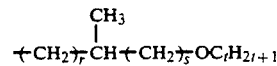

wherein r is 0-7, s is 0 or 1 and t is 1-14 (optically active or inactive); and (iv)

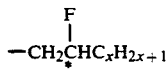
wherein x is 1-16. Herein * denotes an optically active center.
The mesomorphic compounds represented by the general formula (I) may be synthesized through the following reaction schemes.
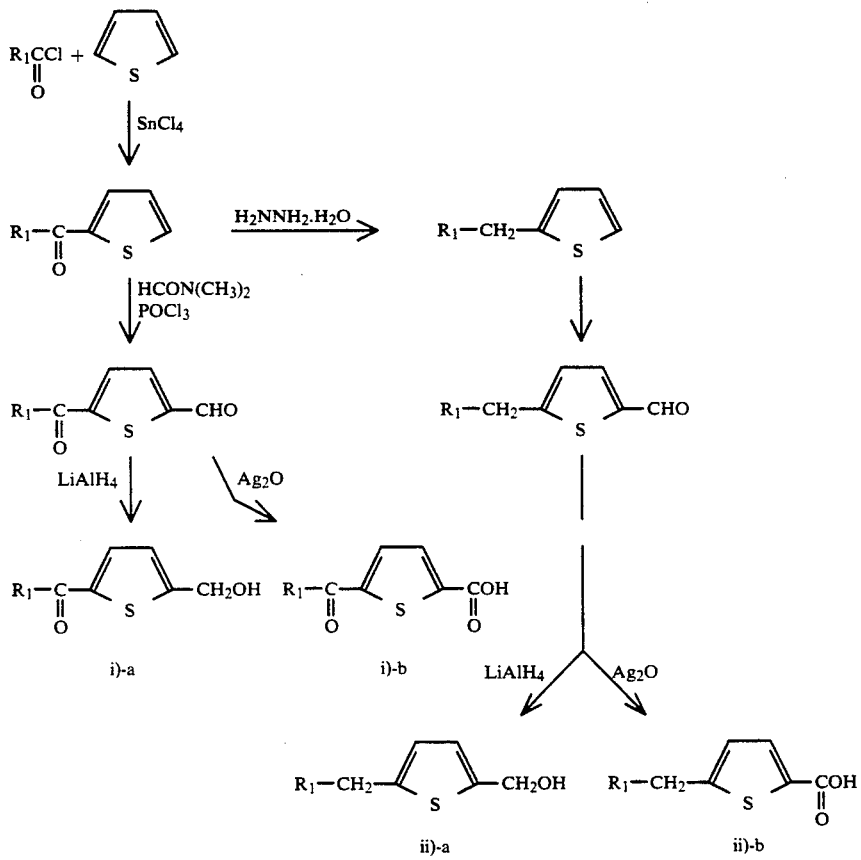
In the above, $R_1$ denotes a linear or branched alkyl group.
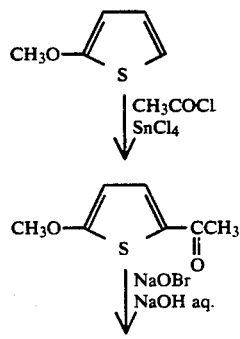

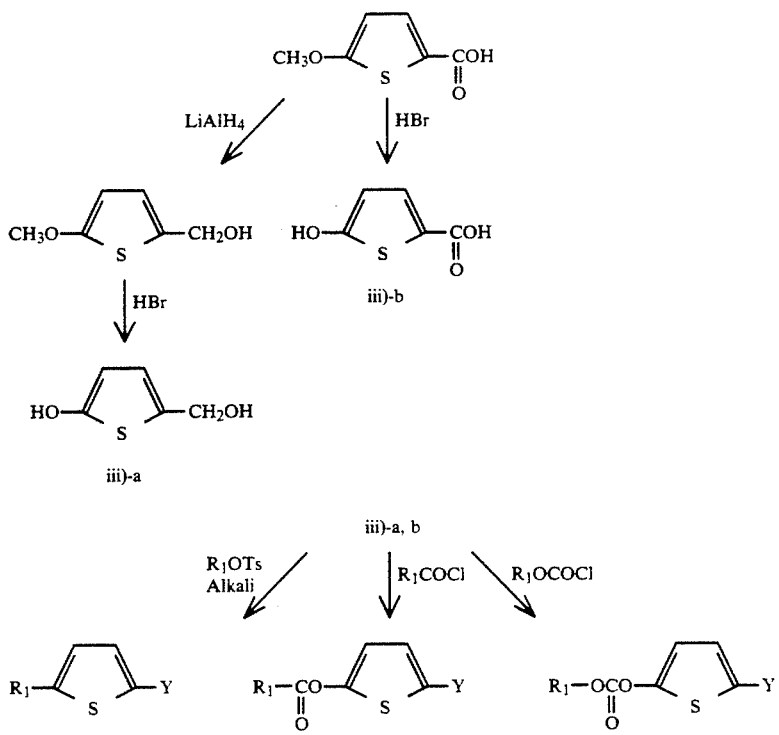
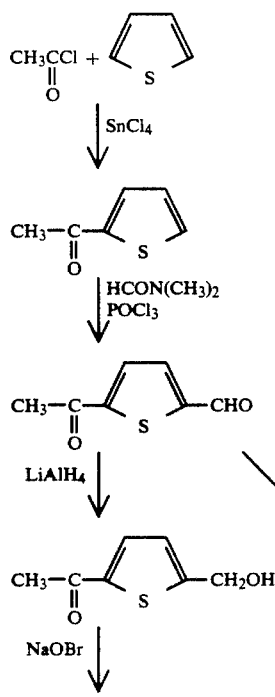
In the above, $R_1$ denotes a linear or branched alkyl group and Y denotes —$CH_2OH$ or —COOH.
(Case where X is —OC—
              ‖
              O )
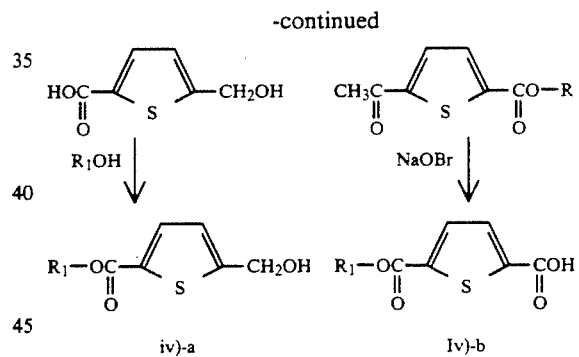
In the above, $R_1$ denotes a linear or branched alkyl group.
(case where Z is —O—, —OC— or —OCO—
                     ‖        ‖
                     O        O )
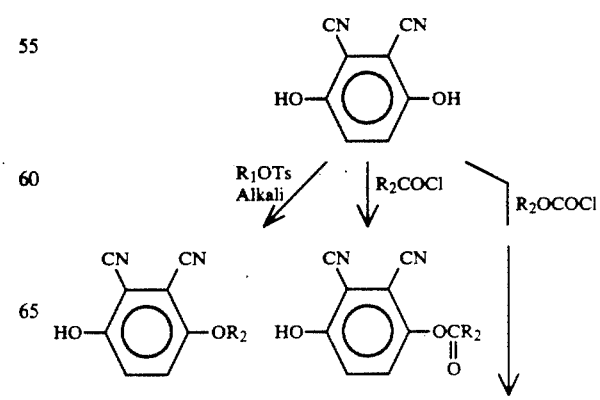

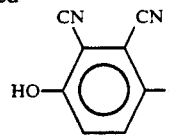 5
In the above, R₂ denotes a linear or branched alkyl group.
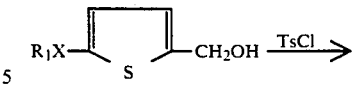
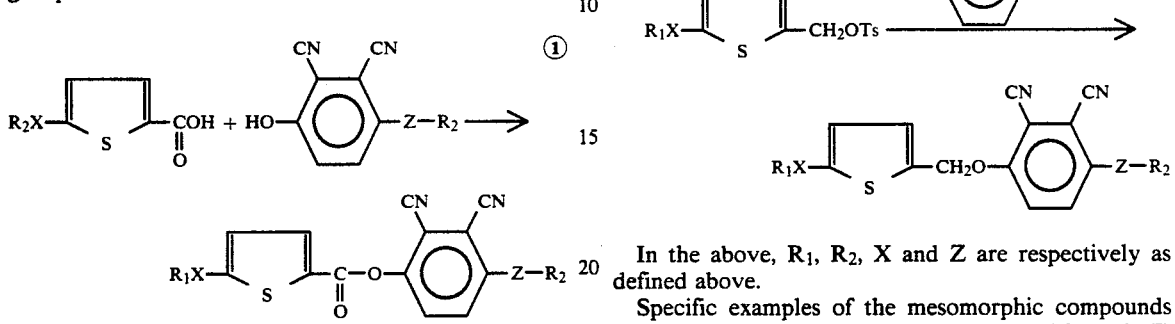
In the above, $R_1$, $R_2$, X and Z are respectively as defined above.
Specific examples of the mesomorphic compounds represented by the above-mentioned general formula (I) may includes those shown by the following structural formulas.
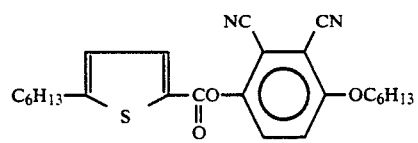 1-1
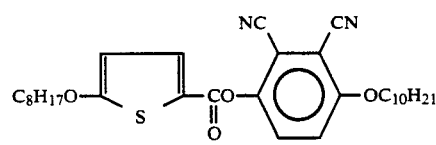 1-2
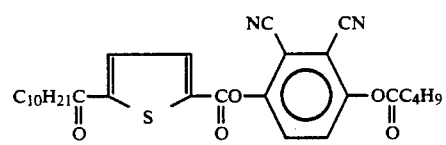 1-3
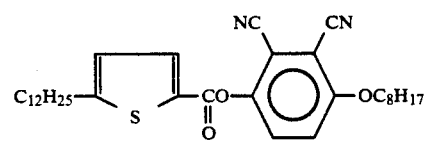 1-4
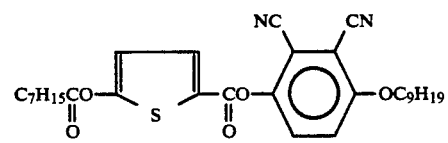 1-5
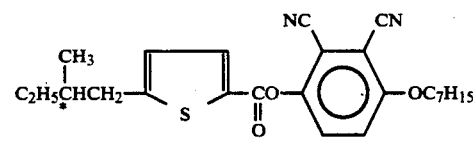 1-6
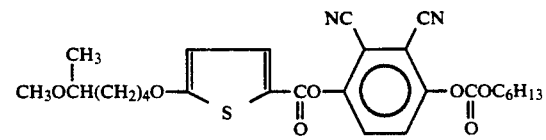 1-7

-continued
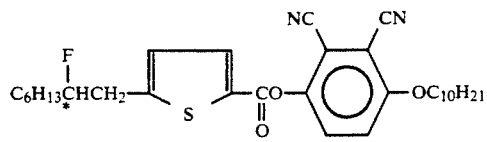
1-8
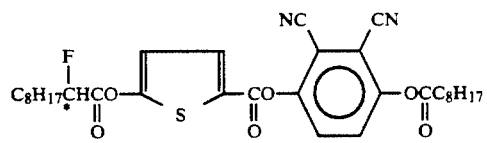
1-9
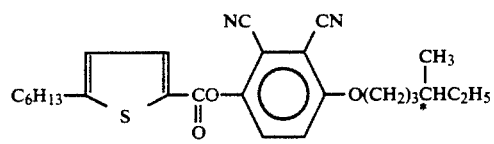
1-10
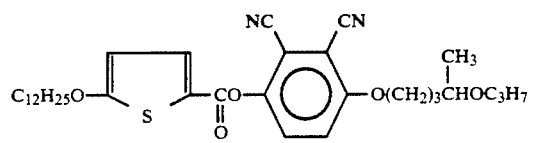
1-11
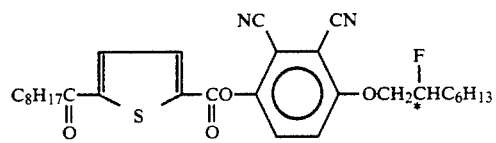
1-12
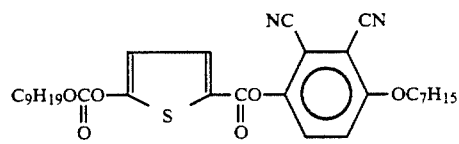
1-13
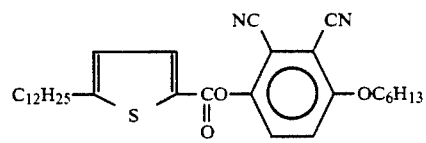
1-14
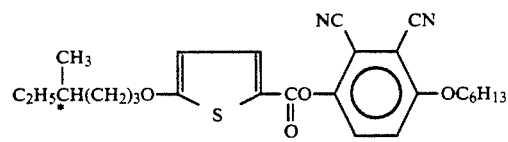
1-15
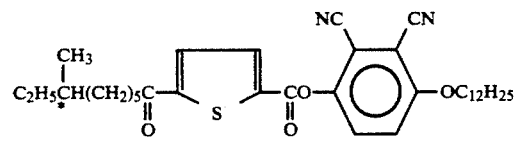
1-16
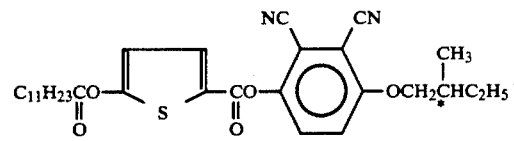
1-17
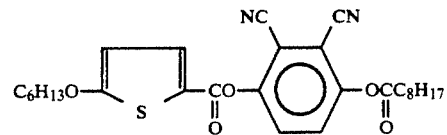
1-18

-continued
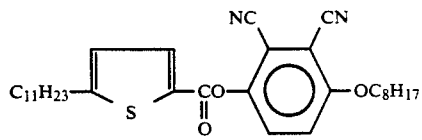
1-19
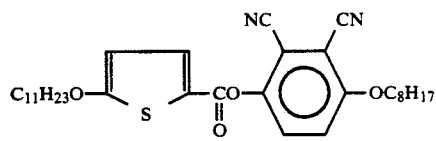
1-20
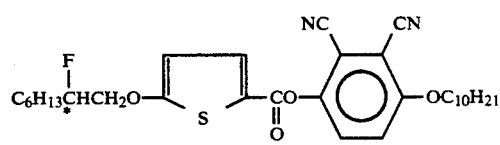
1-21
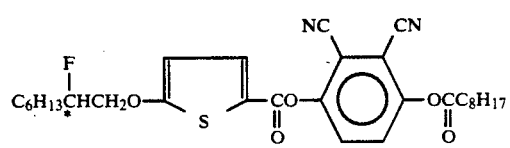
1-22
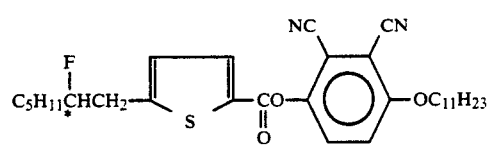
1-23
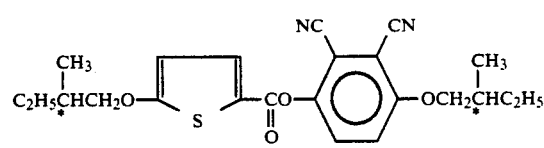
1-24
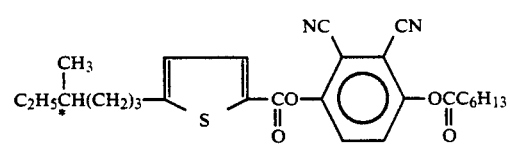
1-25
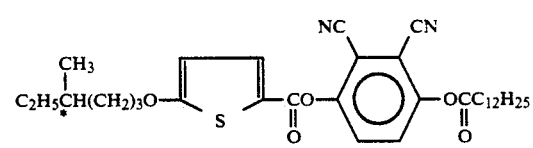
1-26
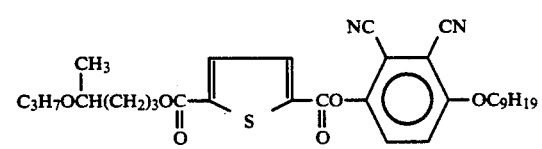
1-27
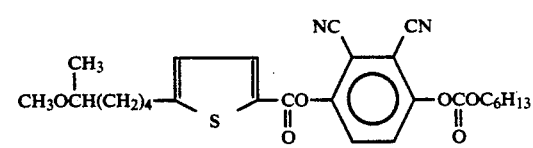
1-28
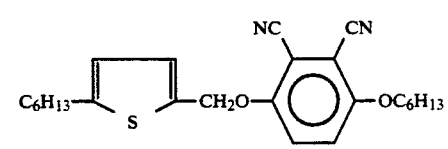
1-29

-continued
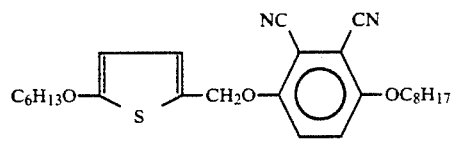 1-30
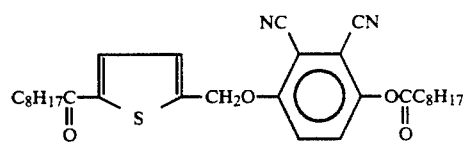 1-31
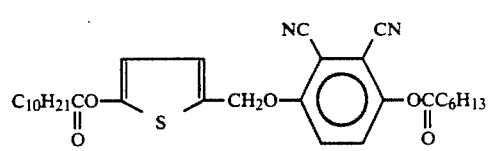 1-32
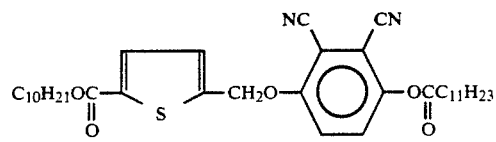 1-33
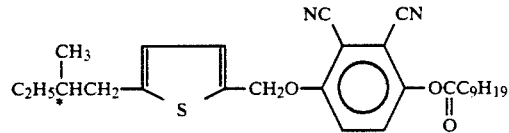 1-34
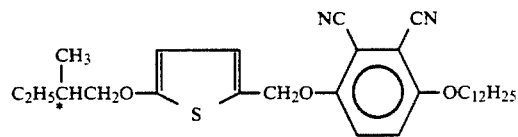 1-35
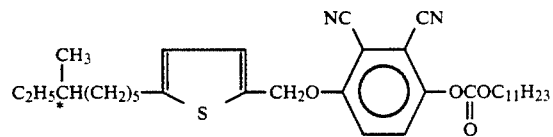 1-36
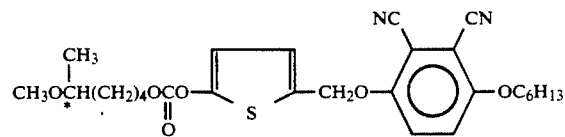 1-37
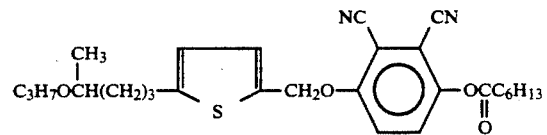 1-38
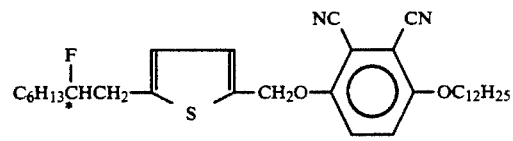 1-39
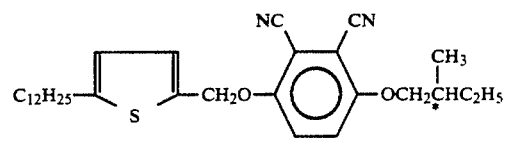 1-40

-continued (1-41) C6H13-[thiophene]-CH2O-[phenyl(NC,CN)]-OCH2*CHFC8H17

(1-42) C8H17CO-[thiophene]-CH2O-[phenyl(NC,CN)]-O(CH2)2CH(CH3)OCH3

(1-43) C9H19OCO-[thiophene]-CH2O-[phenyl(NC,CN)]-OC(=O)(CH2)2*CH(CH3)OC3H7

The liquid crystal composition according to the present invention may be obtained by mixing at least one species of the compound represented by the formula (I) and another mesomorphic compound in appropriate proportions. The liquid crystal composition according to the present invention may preferably be formulated as a ferroelectric liquid crystal composition, particularly a ferroelectric chiral smectic liquid crystal composition.

Specific examples of another mesomorphic compound as described above may include those denoted by the following structural formulas.

(1) $C_{12}H_{25}$–[pyrimidine]–[phenyl]–OCH$_2$*CH(CH$_3$)C$_2$H$_5$ (2) $C_{10}H_{21}O$–[phenyl]–CO-O–[phenyl]–CO-O*CH(CH$_3$)C$_2$H$_5$ (3) $C_8H_{17}O$–[phenyl]–CO-O–[phenyl]–CO-O*CH$_2$CH(CH$_3$)C$_2$H$_5$ (4) $C_{11}H_{23}O$–[pyrimidine]–[phenyl]–OCH$_2$*CH(CH$_3$)C$_2$H$_5$ (5) $C_8H_{17}O$–[phenyl]–O-CO–[phenyl]–O(CH$_2$)$_3$*CH(CH$_3$)C$_2$H$_5$ (6) $C_9H_{19}OCO$–[biphenyl]–OCH$_2$*CH(CH$_3$)C$_2$H$_5$ (7) $C_8H_{17}$–[biphenyl]–CO-O–[phenyl]–OCH$_2$*CH(CH$_3$)C$_2$H$_5$ (8) $C_8H_{17}O$–[phenyl]–O-CO–[biphenyl]–CH$_2$*CH(CH$_3$)C$_2$H$_5$ (9) $C_8H_{17}O$–[phenyl]–C(=S)–[phenyl]–CH$_2$*CH(CH$_3$)C$_2$H$_5$

(10) $C_{13}H_{27}$–[biphenyl]–C(=S)–[phenyl]–CH$_2$*CH(CH$_3$)C$_2$H$_5$

(11) $C_{16}H_{33}O$–[phenyl]–C(=S)–[phenyl]–OCH$_2$*CH(CH$_3$)C$_3$H$_7$

-continued $$C_7H_{15}O-\phenyl-\phenyl-\underset{O}{C}O-\phenyl-\underset{O}{C}OCH_2\overset{*}{C}H(CH_3)C_2H_5 \quad (12)$$

$$C_{10}H_{21}O-\pyrimidine-\phenyl-O(CH_2)_3\overset{*}{C}H(CH_3)C_2H_5 \quad (13)$$

$$C_6H_{13}O-\phenyl-\phenyl-\underset{O}{C}O-\phenyl(F)-O\overset{*}{C}H(CH_3)C_2H_5 \quad (14)$$

$$C_8H_{17}O-\phenyl-pyridine-\underset{O}{C}O-\phenyl-O\overset{*}{C}H(CH_3)C_2H_5 \quad (15)$$

$$C_{12}H_{25}-\phenyl-pyridine-\underset{O}{C}O-\phenyl-\underset{O}{C}OCH_2\overset{*}{C}H(CH_3)C_2H_5 \quad (16)$$

$$C_{12}H_{25}O-\phenyl-pyrazine-\underset{O}{C}O(CH_2)_3\overset{*}{C}H(CH_3)C_2H_5 \quad (17)$$

$$C_8H_{17}O-\phenyl-\underset{O}{C}O-\phenyl-O\overset{*}{C}H_2CH(CH_3)C_2H_5 \quad (18)$$

$$C_{10}H_{21}O-\phenyl-\underset{O}{C}O-\phenyl-O\overset{*}{C}H(CH_3)C_2H_5 \quad (19)$$

$$C_{10}H_{21}O-pyridine-\phenyl-O(CH_2)_3\overset{*}{C}H(CH_3)C_2H_5 \quad (20)$$

$$C_8H_{17}-pyrazine-\phenyl-O(CH_2)_3\overset{*}{C}H(CH_3)C_2H_5 \quad (21)$$

$$C_7H_{15}O-\phenyl-O\underset{O}{C}-\phenyl-O(CH_2)_3\overset{*}{C}H(CH_3)C_3H_7 \quad (22)$$

$$C_8H_{17}-pyrimidine-\phenyl-O(CH_2)_3\overset{*}{C}H(CH_3)C_2H_5 \quad (23)$$

$$C_{11}H_{23}O-pyridine-\phenyl-O(CH_2)_2\overset{*}{C}H(CH_3)C_2H_5 \quad (24)$$

$$C_{12}H_{25}-pyrimidine-\phenyl-O\underset{O}{C}-\phenyl-O(CH_2)_3\overset{*}{C}H(CH_3)C_2H_5 \quad (25)$$

$$C_8H_{17}-\phenyl-OCH_2-\phenyl-\phenyl-CH_2\overset{*}{C}H(CH_3)C_2H_5 \quad (26)$$

$$C_8H_{17}-\phenyl-O\underset{O}{C}-\phenyl-\phenyl-O\overset{*}{C}H(CH_3)C_6H_{13} \quad (27)$$

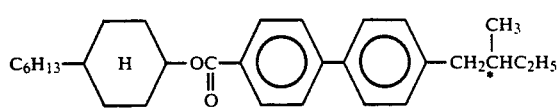 (28)
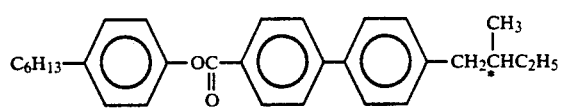 (29)
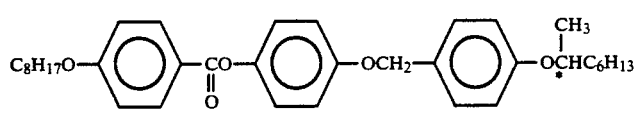 (30)
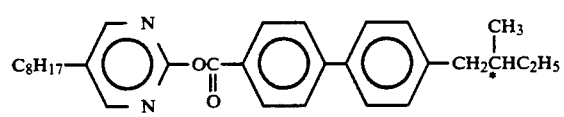 (31)
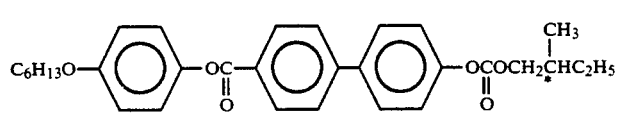 (32)
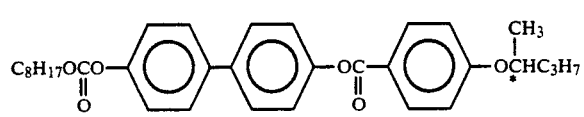 (33)
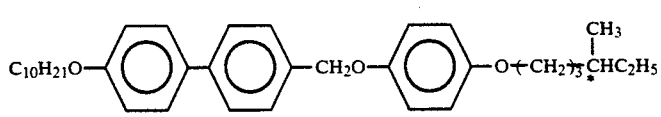 (34)
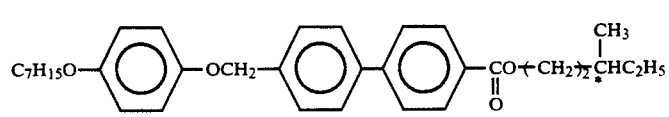 (35)
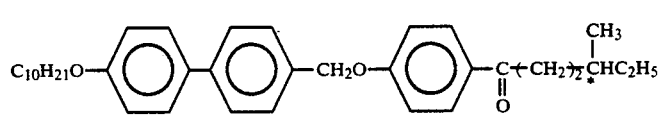 (36)
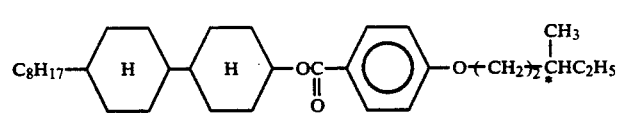 (37)
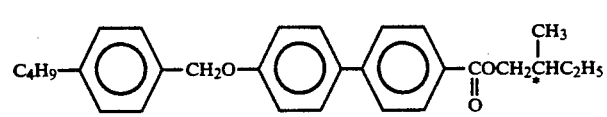 (38)
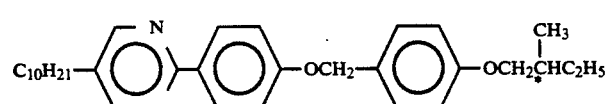 (39)
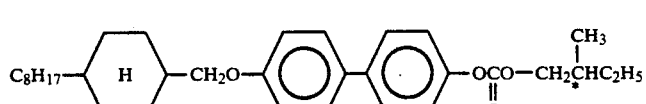 (40)

-continued
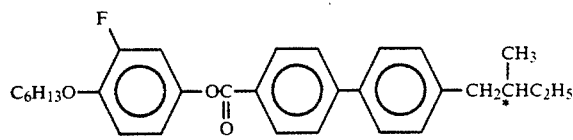
(41)
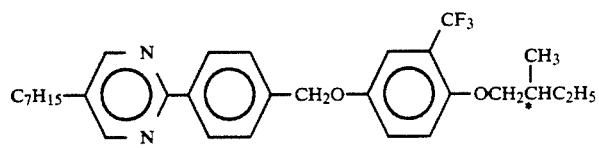
(42)
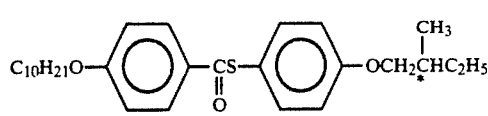
(43)
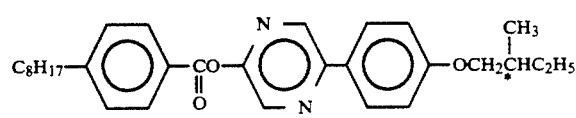
(44)
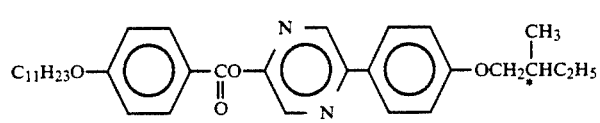
(45)
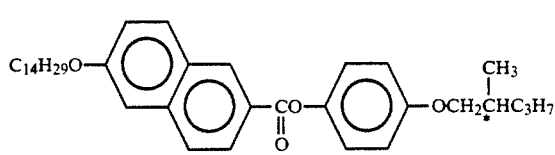
(46)
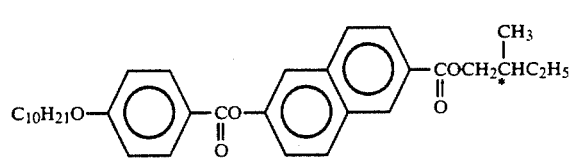
(47)
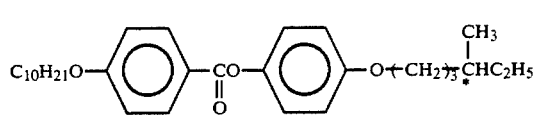
(48)
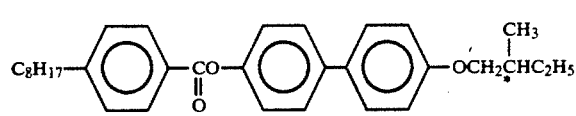
(49)
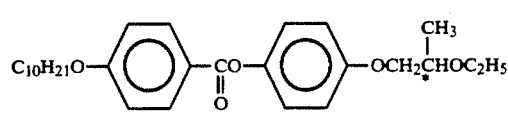
(50)
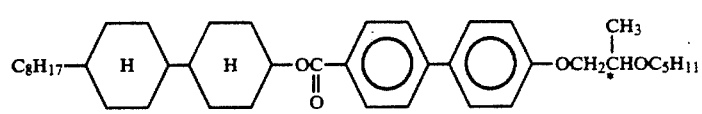
(51)
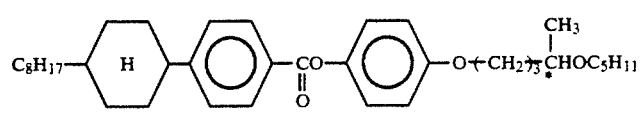
(52)

-continued
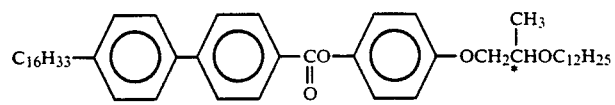 (53)
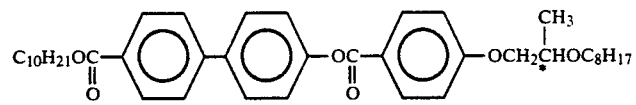 (54)
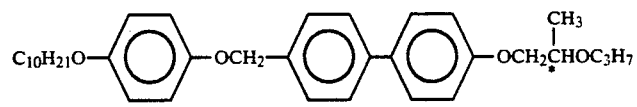 (55)
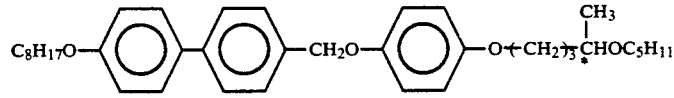 (56)
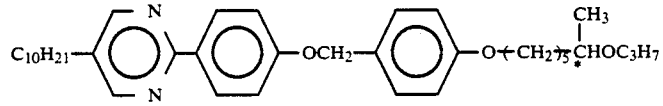 (57)
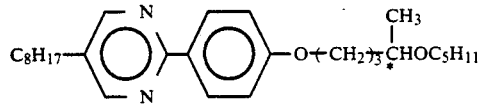 (58)
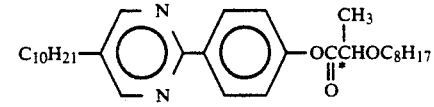 (59)
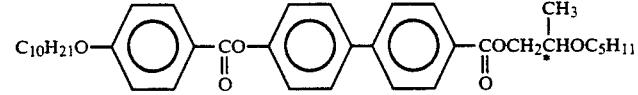 (60)
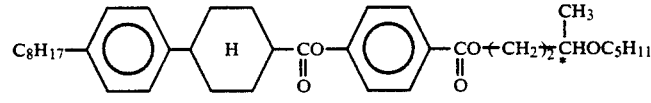 (61)
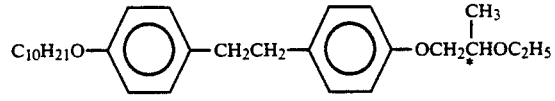 (62)
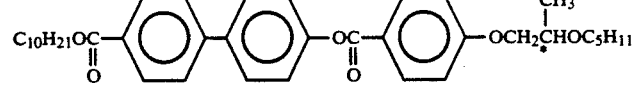 (63)
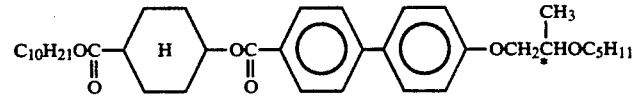 (64)
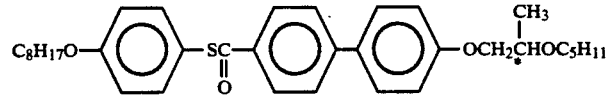 (65)
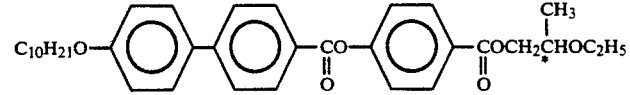 (66)

-continued
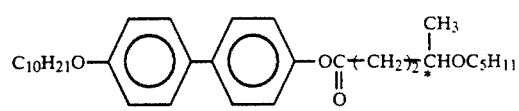 (67)
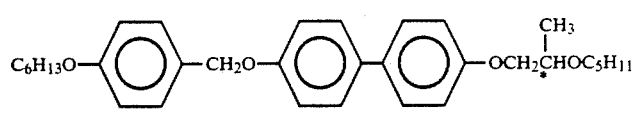 (68)
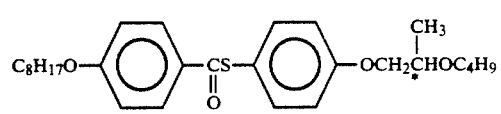 (69)
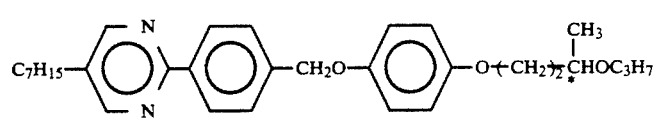 (70)
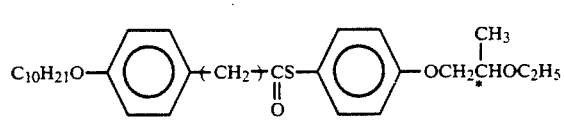 (71)
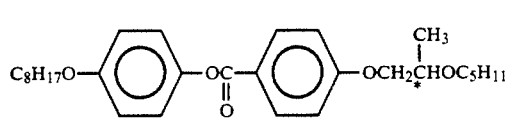 (72)
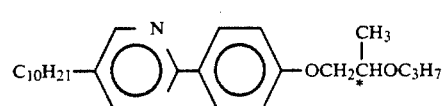 (73)
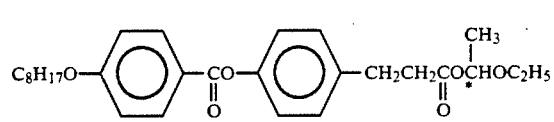 (74)
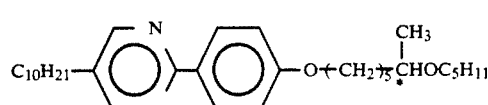 (75)
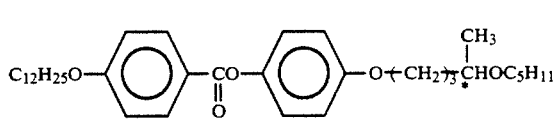 (76)
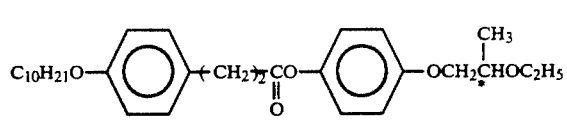 (77)
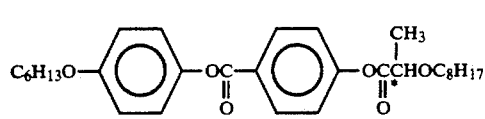 (78)
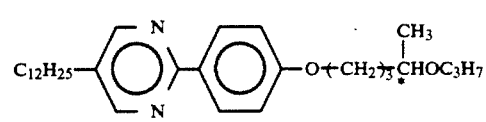 (79)
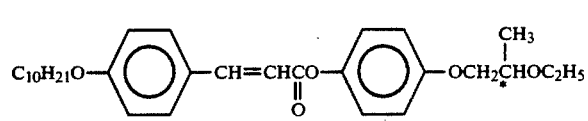 (80)
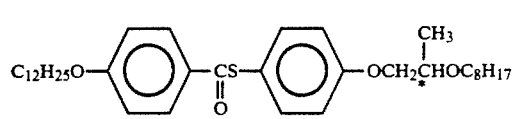 (81)

-continued
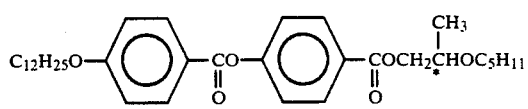 (82)
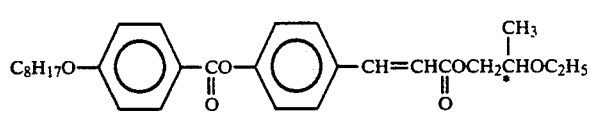 (83)
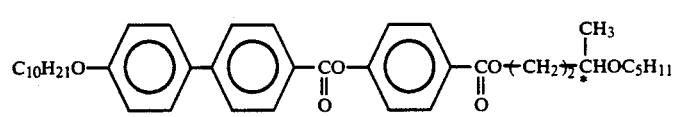 (84)
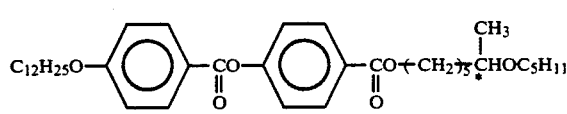 (85)
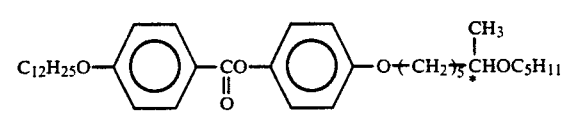 (86)
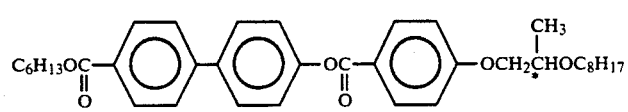 (87)
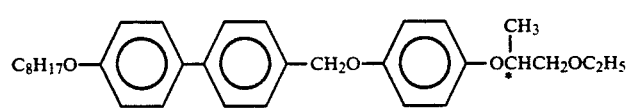 (88)
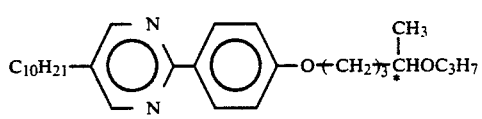 (89)
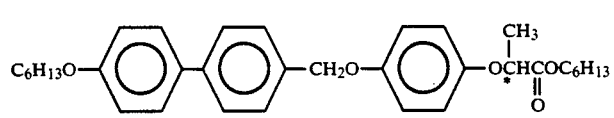 (90)
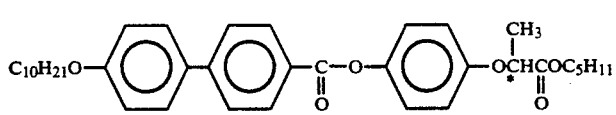 (91)
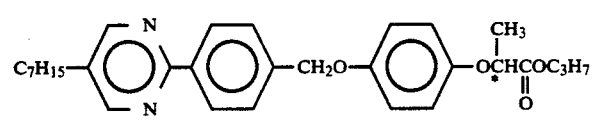 (92)
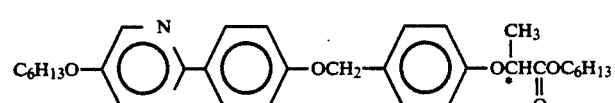 (93)
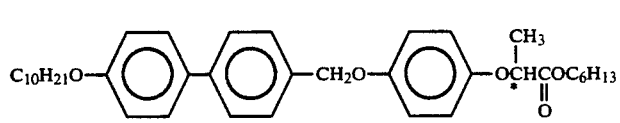 (94)

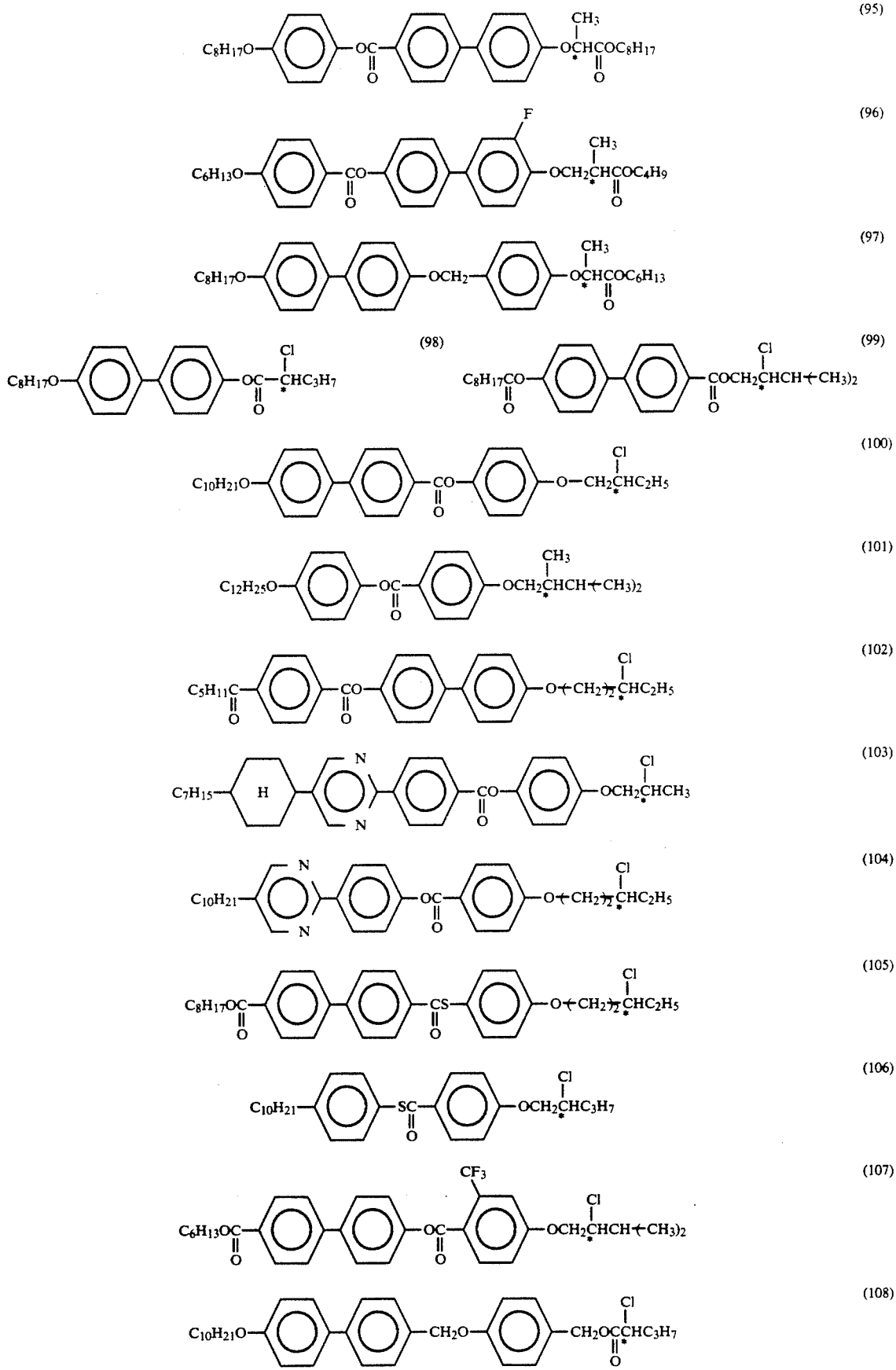

-continued
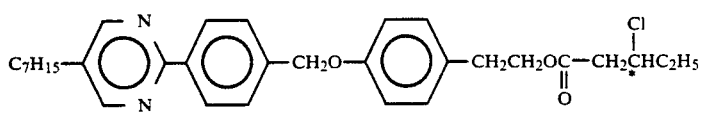 (109)
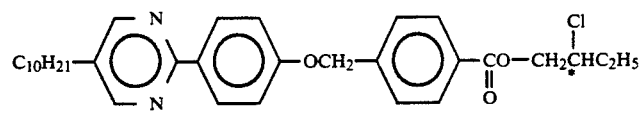 (110)
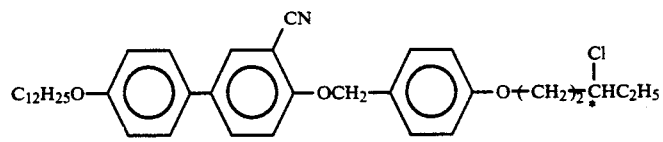 (111)
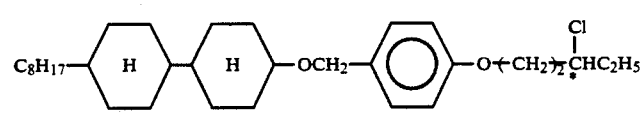 (112)
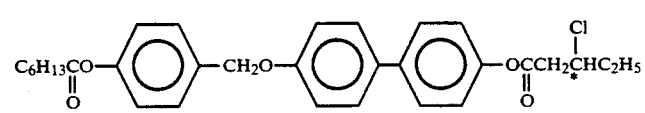 (113)
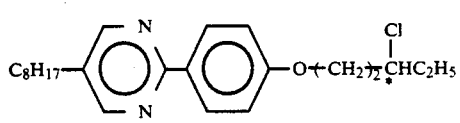 (114)
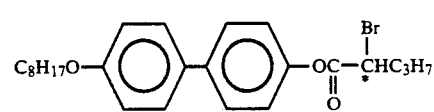 (115)
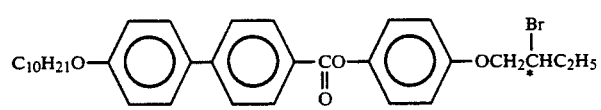 (116)
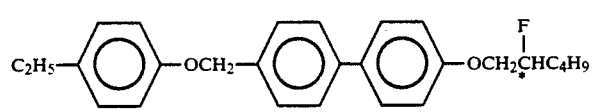 (117)
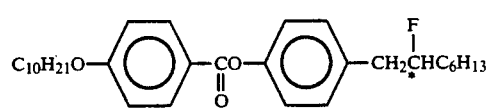 (118)
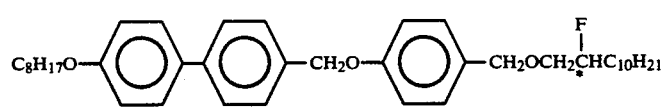 (119)
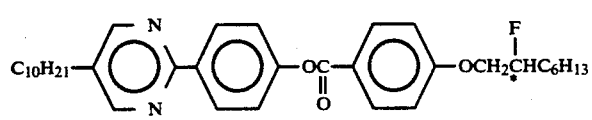 (120)
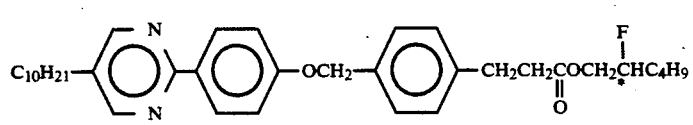 (121)
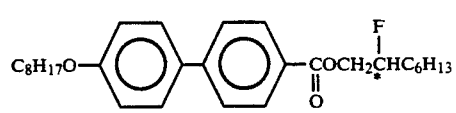 (122)

-continued (123) $C_{10}H_{21}O-\phenyl-\phenyl-COO-\phenyl-OCH_2\overset{*}{C}HC_8H_{17}$ with F on chiral carbon (124) $C_{12}H_{25}O-\phenyl-COO-\phenyl-OCH_2\overset{*}{C}HC_6H_{13}$ with F (125) $C_7H_{15}-\text{cyclohexyl}-\text{pyrimidine}-\phenyl-COCH_2\overset{*}{C}HC_8H_{17}$ with F (126) $C_7H_{15}-\text{pyridine}-\phenyl-COO-\phenyl-OCH_2\overset{*}{C}HC_5H_{11}$ with F (127) $C_6H_{13}O-\phenyl-OOC-\phenyl-OCH_2\overset{*}{C}HC_8H_{17}$ with F (128) $C_8H_{17}O-\phenyl-SO-\phenyl-OCH_2\overset{*}{C}HC_6H_{13}$ with F (129) $C_{10}H_{21}-\text{pyrimidine}-\phenyl-OCH_2\overset{*}{C}HC_8H_{17}$ with F (130) $C_5H_{11}-\text{cyclohexyl}-COO-\phenyl-OCH_2\overset{*}{C}HC_6H_{13}$ with F (131) $C_8H_{17}O-\phenyl-COO-\phenyl-OCH_2\overset{*}{C}HC_2H_5$ with F (132) $C_8H_{17}-\text{pyrimidine}-\phenyl-OCH_2\overset{*}{C}HC_2H_5$ with F (133) $C_8H_{17}O-\phenyl-CH=CHCO-O-\phenyl-COCH_2\overset{*}{C}HC_6H_{13}$ with F (134) $C_{13}H_{27}O-\phenyl-COO-\phenyl-COCH_2\overset{*}{C}HC_6H_{13}$ with F (135) $H_5C_2\overset{CH_3}{CH}(CH_2)_3O-\phenyl-COO-\phenyl-OCH_2\overset{*}{C}HC_6H_{13}$ with F (136) $C_8H_{17}O-\phenyl-COO-\phenyl-OCH_2\overset{*}{C}HC_5H_{11}$ with F (137) $C_{10}H_{21}O-\phenyl-SO-\phenyl-OCH_2\overset{*}{C}HC_8H_{17}$ with F (138) $C_3H_7\overset{CH_3}{CH}CO-O-\phenyl-\phenyl-OCH_2\overset{*}{C}HC_8H_{17}$ with F (139) $C_6H_{13}OOC-\phenyl-\phenyl-O-OC-\phenyl-OCH_2\overset{*}{C}HC_6H_{13}$ with F -continued
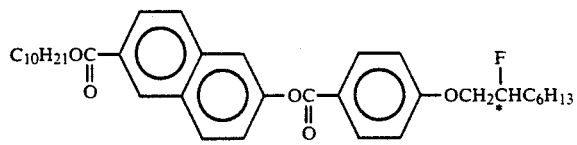 (140)
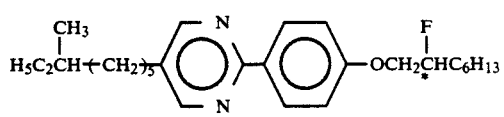 (141)
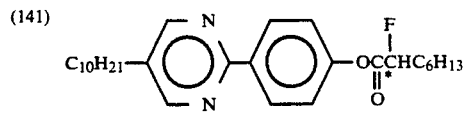 (142)
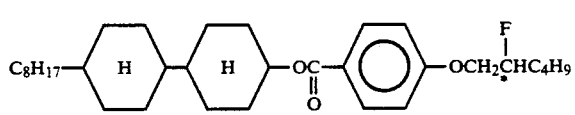 (143)
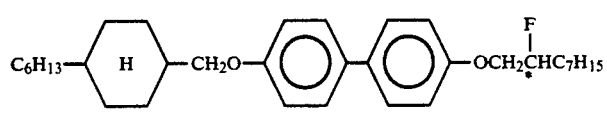 (144)
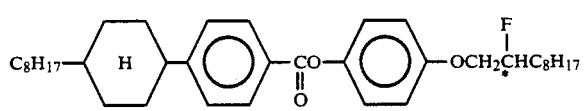 (145)
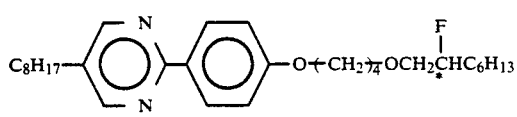 (146)
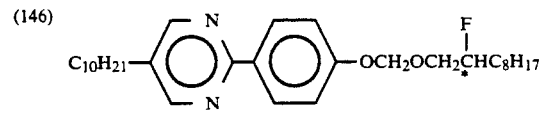 (147)
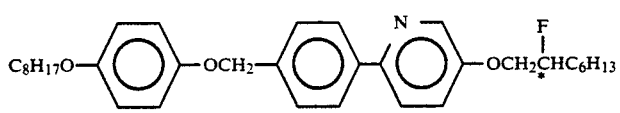 (148)
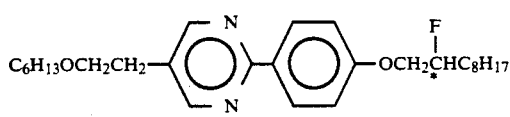 (149)
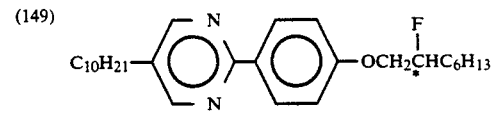 (150)
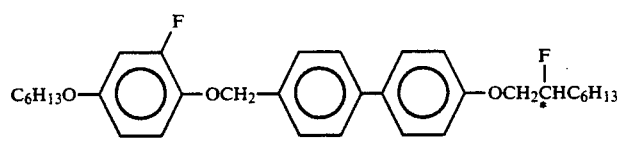 (151)
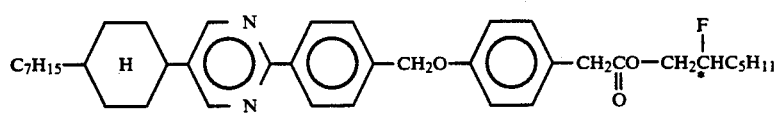 (152)
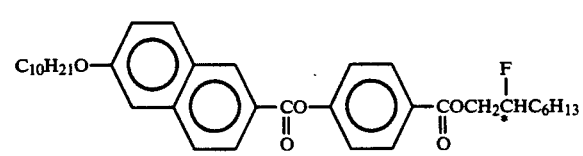 (153)
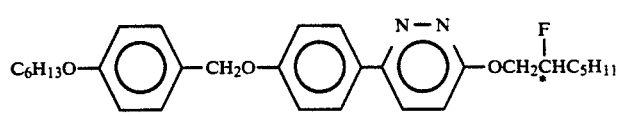 (154)

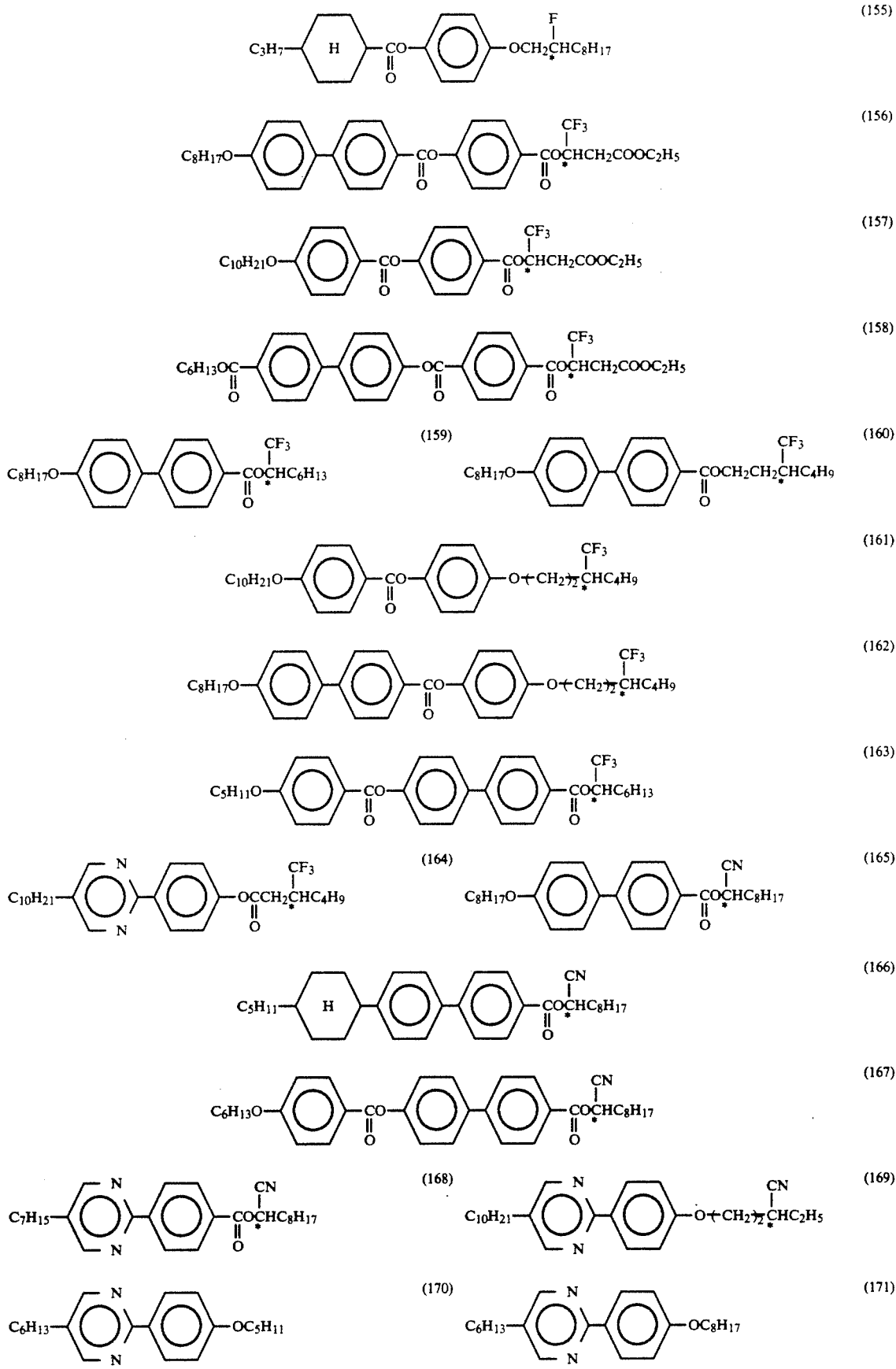

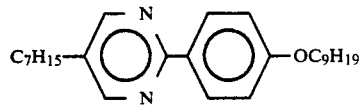
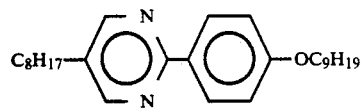
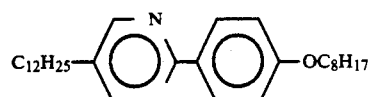
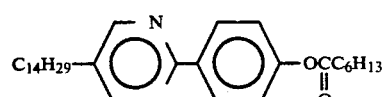
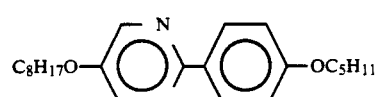
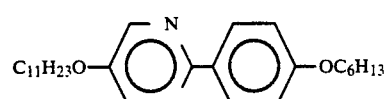
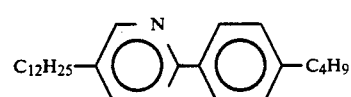
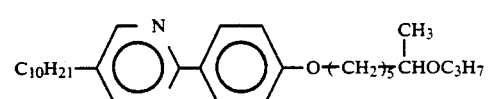
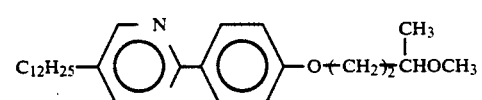
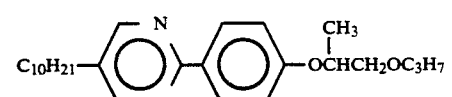
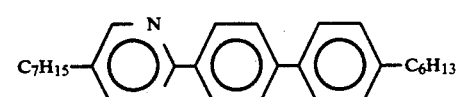
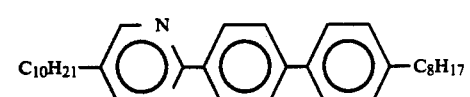
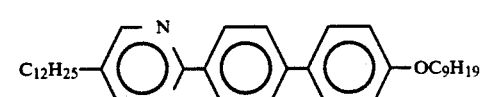

-continued
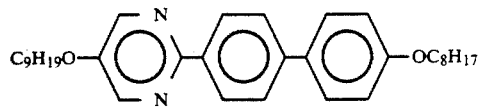 (198)
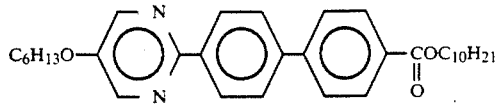 (199)
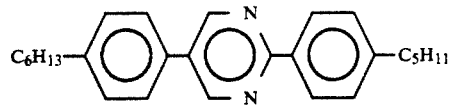 (200)
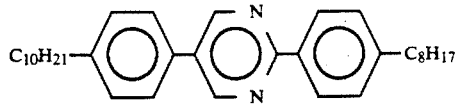 (201)
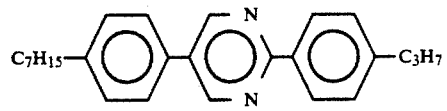 (202)
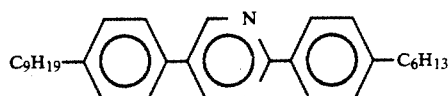 (203)
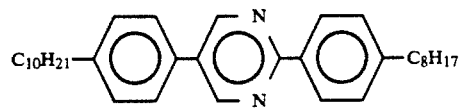 (204)
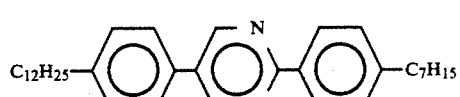 (205)
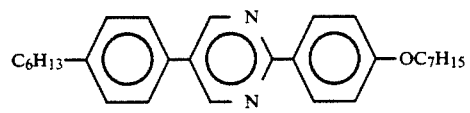 (206)
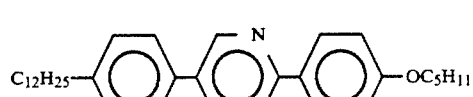 (207)
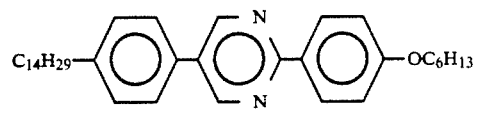 (208)
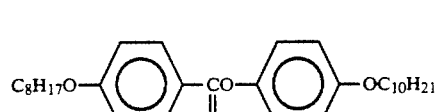 (209)
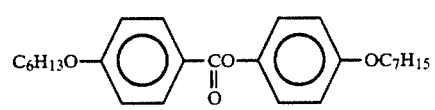 (210)
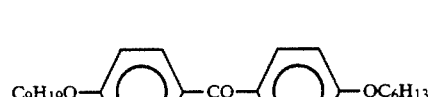 (211)
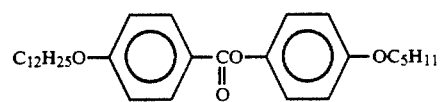 (212)
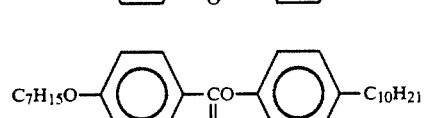 (213)
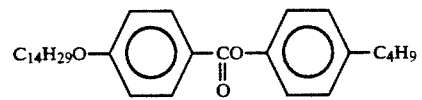 (214)
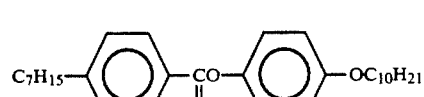 (215)
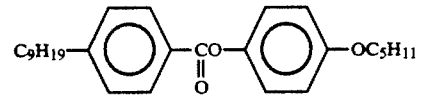 (216)
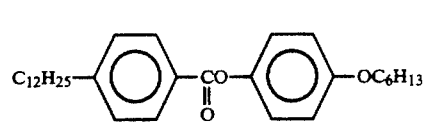 (217)
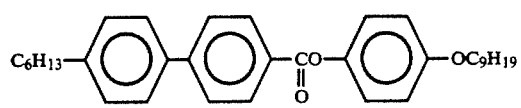 (218)
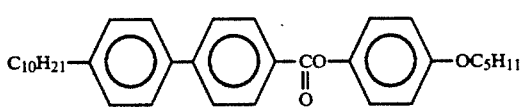 (219)
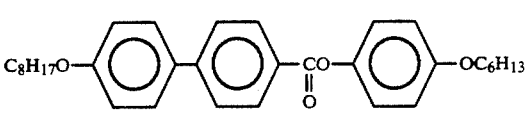 (220)

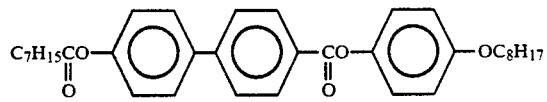
(221)
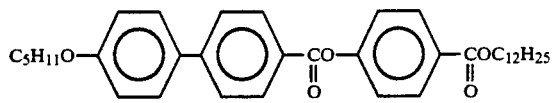
(222)
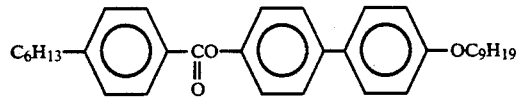
(223)
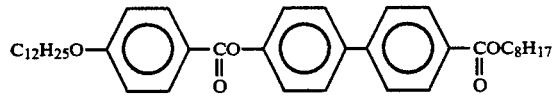
(224)
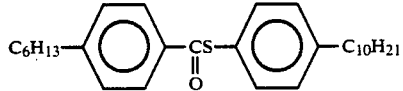
(225)
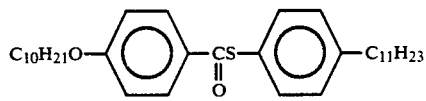
(226)
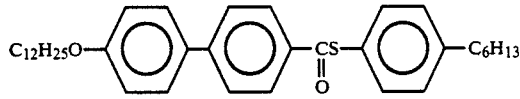
(227)
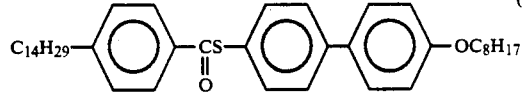
(228)
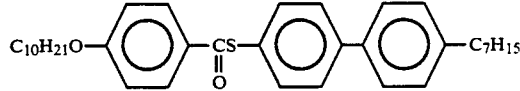
(229)
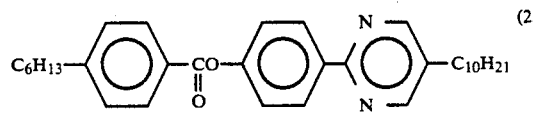
(230)
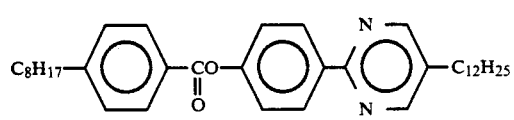
(231)
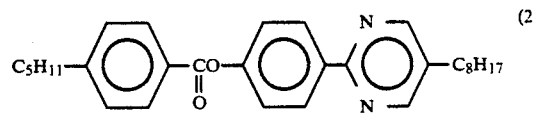
(232)
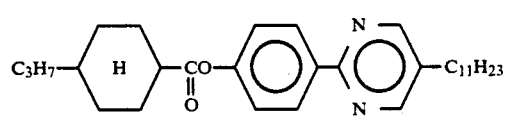
(233)
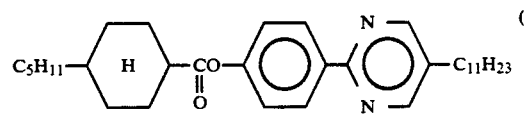
(234)
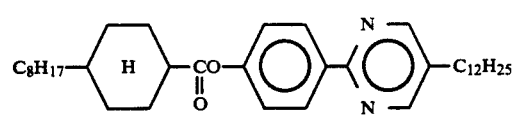
(235)
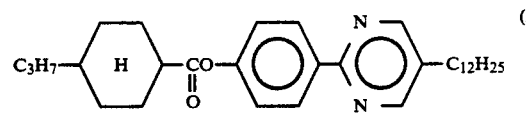
(236)
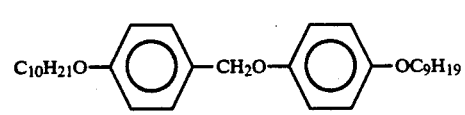
(237)
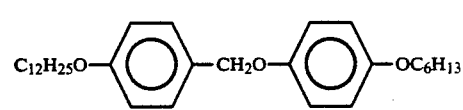
(238)
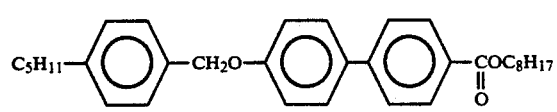
(239)
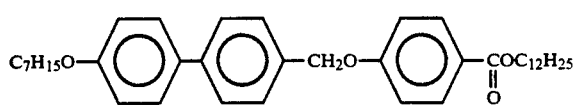
(240)

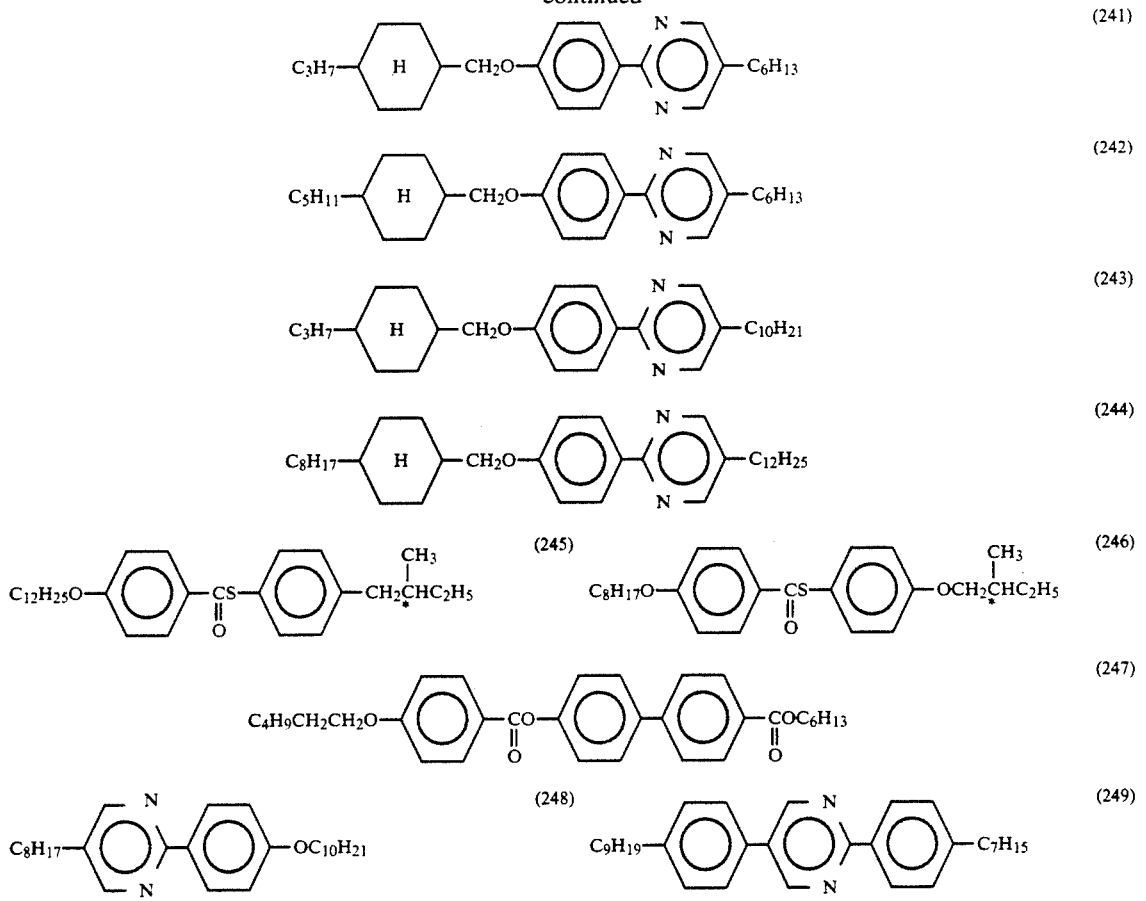

In formulating the liquid crystal composition according to the present invention, it is desirable to mix 1-500 wt. parts preferably 2-100 wt. parts, of a compound represented by the formula (I) with 100 wt. parts of at least one species of another mesomorphic compound as mentioned above or a liquid crystal composition containing another mesomorphic compound (hereinafter, simply referred to as "liquid crystal material").

Further, when two or more species of the compounds represented by the formulas (I) are used, the two or more species of the compound of the formula (I) may be used in a total amount of 1-500 wt. parts, preferably 2-100 wt. parts, per 100 wt. parts of the liquid crystal material.

The ferroelectric liquid crystal device according to the present invention may preferably be prepared by heating the liquid crystal composition prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the ferroelectric liquid crystal device prepared as described above for explanation of the structure thereof.

Referring to FIG. 1, the ferroelectric liquid crystal device includes a ferroelectric liquid crystal layer 1 disposed between a pair of glass substrates 2 each having thereon a transparent electrode 3 and an insulating alignment control layer 4. Lead wires 6 are connected to the electrodes so as to apply a driving voltage to the liquid crystal layer 1 from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a selection of an organic insulating material or a precursor thereof in a concentration of 0.1 to 20 wt. %, preferably 0.2-10 wt. %, by spinner coating, dip coating, screen printing, spray coating or roller coating, followed by curing or hardening under prescribed hardening condition (e.g., by heating). The insulating alignment control layer may have a thickness of ordinarily 30 Å-1 micron, preferably 30-3000 Å, further preferably 50-1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a ferroelectric liquid crystal is sealed up to provide a ferroelectric liquid crystal layer 1 in a thickness of generally 0.5 to 20 microns, preferably 1 to 5 microns.

The ferroelectric liquid crystal provided by the composition of the present invention may desirably assume a SmC* phase (chiral smectic C phase) in a wide temperature range including room temperature (particularly, broad in a lower temperature side) and also shows a high-speed responsiveness, small temperature-dependence of response speed and wide drive voltage margin when contained in a device.

Particularly, in order to show a good alignment characteristic to form a uniform monodomain, the ferroelectric liquid crystal may show a phase transition series comprising isotropic phase—Ch phase (cholesteric phase)—SmA phase (smectic A phase)—SmC* phase (chiral smectic C phase) on temperature decrease.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

Figure 2:
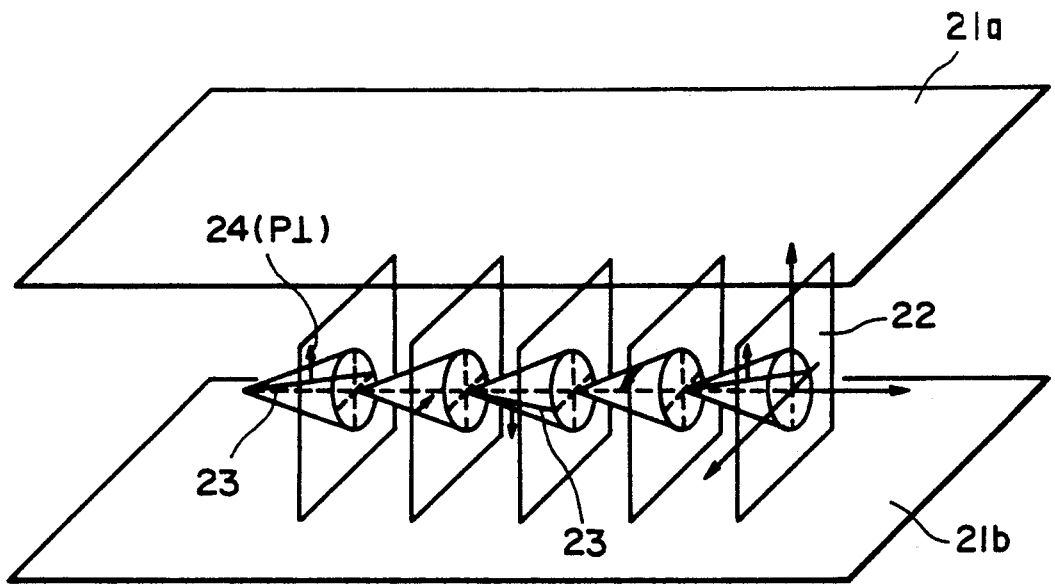
FIGS. 2 and 3 are schematic perspective views of a device cell embodiment for illustrating the operation principle of a ferroelectric liquid crystal device.

FIG. 2 is a schematic illustration of a ferroelectric liquid crystal cell (device) for explaining operation thereof. Reference numerals 21a and 21b denote substrates (glass plates) on which a transparent electrode of, e.g., In$_2$O$_3$, SnO$_2$, ITO (indium-tin-oxide), etc., is disposed, respectively. A liquid crystal of an SmC*-phase (chiral smectic C phase) or SmC*-phase (chiral smectic H phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment (P⊥) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments (P⊥) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
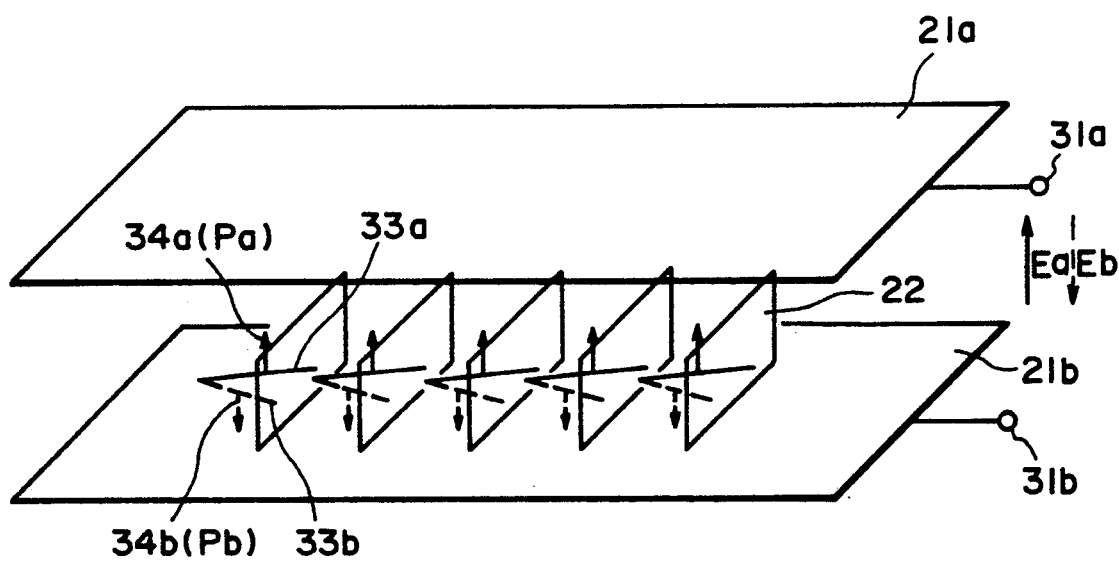
Figure 4:
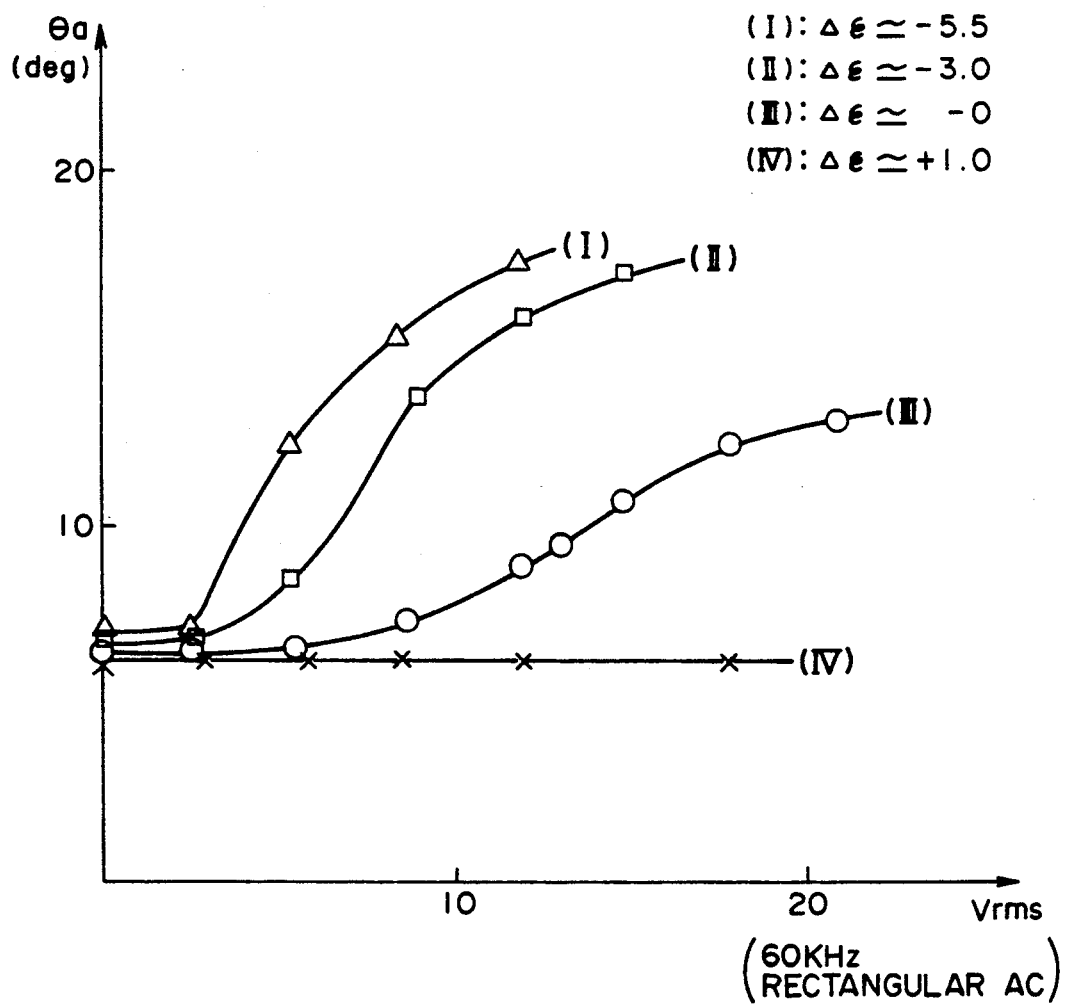
FIG. 4 is a graph showing changes in $\theta a$ versus Vrms with respect to several FLC's having different values of $\Delta\epsilon$.

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

When such a ferroelectric liquid crystal device comprising a ferroelectric liquid crystal composition as described above between a pair of electrode plates is constituted as a simple matrix display device, the device may be driven by a driving method as disclosed in Japanese Laid-Open Patent Applications (KOKAI) Nos. 193426/1984, 193427/1984, 156046/1985, 156047/1985, etc.

Hereinbelow, the present invention will be explained more specifically with reference to examples. It is however to be understood that the present invention is not restricted to these examples.

EXAMPLE 1

2,3-dicyano-4-hexyloxyphenyl 5-hexylthiophene-2-carboxylate (Example Compound No. 1-1) was synthesized through the following steps i(-vi).

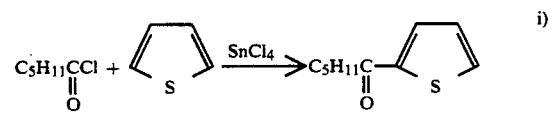

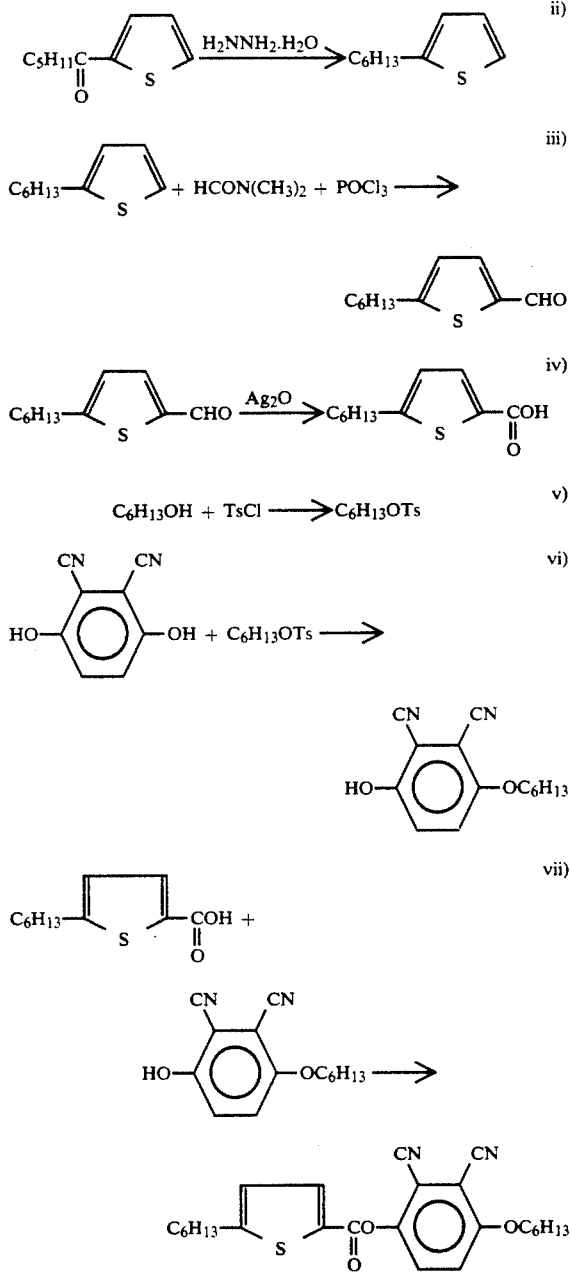

lation in an atmosphere of nitrogen to obtain 313.4 g of a pure product (yield: 77.2%).

Step ii) Production of 2-hexylthiophene

In a 10 liter-five-necked flask, 300 g (1.65 mol) of 2-hexanoylthiophene, 582.1 ml of 60% hydrazine hydrate and 5 liter of diethyleneglycol were placed and reacted for 2 hours at 180° C. with distilling-off of excessive water and hydrazine hydrate. The mixture was cooled to 110° C. and 313.7 g of KOH was added thereto, followed by heating again for 2 hours of reaction at 180° C. After the reaction, the reaction mixture was poured into 10 liter of water, extracted two times with 2 liter of isopropyl ether and washed four times with 2 liter of water, followed by drying with $CaCl_2$ and distilling-off of the solvent to obtain 285 g of a crude product. The crude product was subjected to reduced-pressure distillation in an atmosphere of nitrogen to obtain 230 g of a pure product (yield: 83%).

Step iii) Production of 5-hexylthiophene-2-carbaldehyde

In a 3 liter-four-necked flask, 173.7 (2.38 mol) of N,N-dimethylformamide was placed and cooled to 5° C., followed by addition of 201.4 g (1.31 mol) of $POCl_3$ in 15 min. below 10° C. under stirring. After stirring for 30 min. below 10° C., 200 g (1.19 mol) of 2-hexylthiophene was added dropwise to the mixture in 10 min. at room temperature, followed by stirring for 1.5 hours and further stirring for 2 hours at 60° C. After the reaction, the reaction mixture was poured into 5 liter of iced water, subjected to 3 times of extraction with 2 liter of chloroform and washed 6 times with 2 liter of water. The organic layer was dried with $CaCl_2$, followed by distilling-off of the solvent and reduced-pressure distillation in an atmosphere of nitrogen to obtain 199.2 g of a product (yield: 85.0%). Then, 20 g of the product obtained was purified by silica gel column chromatography with the use of an n-hexane/ethyl acetate=20/1 mixture solvent to obtain 18.2 g of a pure product (yield: 91.0%).

Step iv) Production of 5-hexylthiophene-2-carboxylic acid

In a 500 ml-four-necked flask, 10.0 g ($5.10 \times 10^{-2}$ mol) of 5-hexylthiophene-2-carbaldehyde, 60 ml of ethanol and a solution of 19.0 g of $AgNO_3$ in 60 ml of water were placed. A solution of 10.2 g of NaOH in 300 ml of water was added dropwise to the mixture in 30 min. at room temperature, followed by stirring for 1.5 hours. After the reaction, the reaction mixture was subjected to filtration, and the filtrate was acidified with 6N-HCl to precipitate a crystal. The crystal was recovered by filtration to provide a crude product. The product was subjected to recrystallization from 50% hydrous ethanol to obtain 8.28 g of a pure product (yield: 76.6%).

Step v) Production of n-hexyl p-toluenesulfonate 20 ml of pyridine was added to 5.02 g (49.2 mM) of n-hexanol, followed by stirring below 0° C. To the mixture, 11.24 g (59.0 mM) of p-toluenesulfonyl chloride was added. The mixture was stirred for 6 hours below 0° C. After the reaction, the reaction mixture was poured into iced water and acidified with conc. HCl, followed by two times of extraction with dichloromethane, two times of washing with water, drying with sodium sulfate and distilling-off of the solvent to obtain 12.0 g (46.8 mM) of an objective product (yield: 95.0%).

Step i) Production of 2-hexanoylthiophene

In a 5 liter-five-necked flask, 187.3 g (2.23 mol) of thiophene, 300 g (2.23 mol) of n-hexanoyl chloride and 2.7 liter of dry benzene were placed and cooled below 0° C. To the mixture under stirring, 237.9 g ($9.13 \times 10^{-1}$ mol) of $SnCl_4$ was added dropwise in 1 hour below 0° C. The mixture was stirred for 30 min. below 0° C., followed by stirring for 3.5 hours while being gradually restored to room temperature. After the reaction, 2 liter of 10% HCl was added to the reaction mixture, followed by stirring for 10 min. The separated organic layer was successively washed three times with 500 ml each of 10% HCl, water, 5% $Na_2CO_3$ and water, followed by drying with $CaCl_2$ and distilling-off of the solvent to obtain 408 g of a crude product. The crude product was subjected to reduced-pressure distil-

Step vi) Production of 2,3-dicyanohydroquinone monohexyl ether 11.3 g (44.1 mM) of n-hexyl p-toluenesulfonate was added to the mixture of 5.0 g (31.3 mM) of dicyanohydroquinone and 37.5 ml of 5% NaOH aqueous solution, followed by 7 hours of stirring under refluxing. After the reaction, the reaction mixture was washed with toluene and the aqueous layer was acidified with HCl. The resultant precipitate was recovered through filtration and dried. To the precipitate, 1 liter of toluene was added. After the insoluble substrate was filtered out, the filtrate was subjected to recrystallization in a refrigerator and further subjected to recrystallization from a mixture solvent of water/methanol to obtain 2.1 g of an objective product (yield: 27.5%). m.p.: 150°–153° C.

Step vii) Production of 2,3-dicyano-4-hexyloxyphenyl 5-hexylthiophene-2-carboxylate 0.50 g (2.36 mM) of 5-hexylthiophene-2-carboxylic acid (M.W.: 212), 0.58 g (2.36 mM) of 2,3-dicyanohydroquinone monohexyl ether (M.W.: 244) and 20 ml of THF were mixed and stirred. To the mixture, 0.49 g (2.36 mM) of dicyclohexylcarbodiimide (M.W.: 206) and 0.05 g of pyrrolidinopyridine were added, followed by stirring overnight at room temperature. After the reaction, the reaction mixture was subjected to filtration and the filtrate was subjected to distillation to obtain a crude product. The crude product was purified by silica gel column chromatography with the use of benzene and recrystallized from ethanol to obtain 0.55 g of an objective product (yield: 53.4%).

Phase transition temperature (°C.)

Cryst. $\underset{73.7}{\overset{81.0}{\rightleftarrows}}$ Iso.

Cryst.: crystal, and
Iso.: isotropic phase.

EXAMPLE 2

2,3-dicyano-4-octyloxyphenyl 5-dodecylthiophene-2-carboxylate. (Example Compound No. 1-4) was synthesized through the following steps i)–vi).

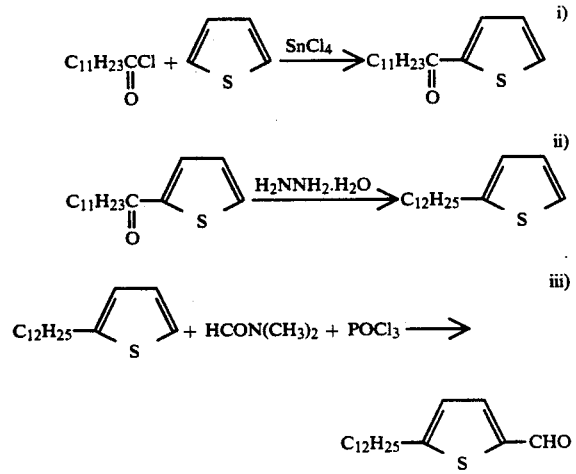

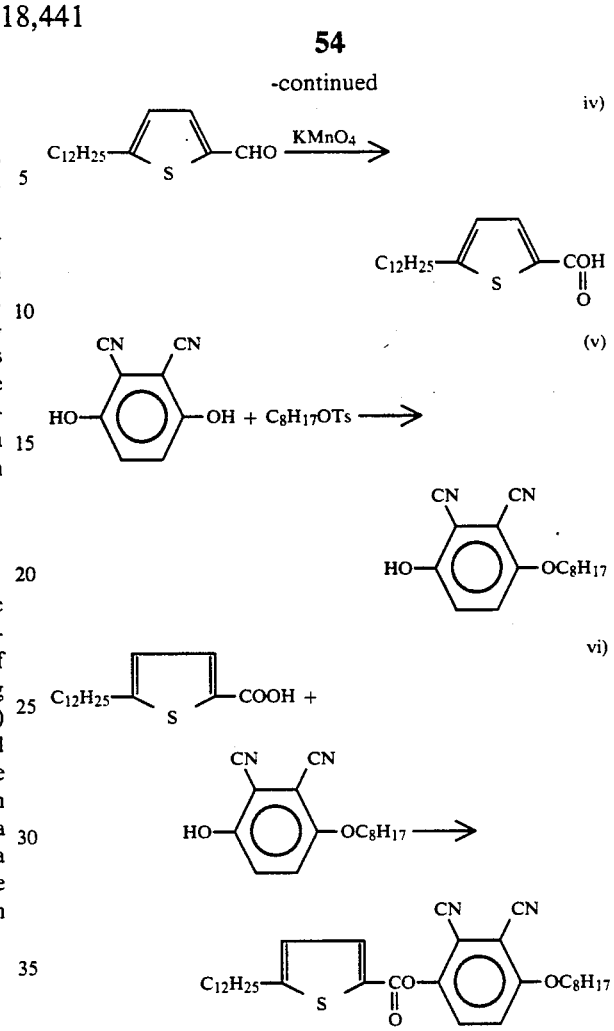

Step i) Production of 2-dodecanoylthiophene

In a 5 liter-five-necked flask, 112.5 g (1.34 mol) of thiophene, 300 g (1.37 mol) of n-dodecanoyl chloride and 2.25 liter of dry benzene were placed and cooled below 0° C. To the mixture under stirring, 148.5 g ($5.70 \times 10^{-1}$ mol) of SnCl$_4$ was added dropwise in 1 hour below 0° C. The mixture was stirred for 30 min. below 0° C., followed by stirring for 4 hours while being gradually restored to room temperature. After the reaction, 2 liter of 10% HCl was added to the reaction mixture, followed by stirring for 10 min. The separated organic layer was successively washed three times with 500 ml each of 10% HCl, water, 5% Na$_2$CO$_3$ and water, followed by drying with CaCl$_2$ and distilling-off of the solvent to obtain 315 g of a crude product. The crude product was subjected to reduced-pressure distillation under an atmosphere of nitrogen to obtain 270 g of a pure product (yield: 75.7%). b.p.: 146° C./0.65 mmHg

Step ii) Production of 2-dodecylthiophene

In a 5 liter-five-necked flask, 266 g (1.0 mol) of 2-dodecanoylthiophene, 392.4 ml of 60% hydrazine hydrate and 3 liter of diethyleneglycol were placed and reacted for 6 hours at 195° C. with distilling-off of excessive water and hydrazine hydrate. The mixture was cooled to 50° C. and 210.6 g of KOH was added thereto, followed by heating again to react for 2.5 hours at 155° C. After the reaction, the reaction mixture was poured into 10 liter of water, extracted two times with 2 liter of isopropyl ether, followed by drying with $CaCl_2$ and distilling-off of the solvent to obtain 229 g of a crude product. The crude product was subjected to reduced-pressure distillation in an atmosphere of nitrogen to obtain 168 g of a pure product (yield: 66.7%). b.p.: 121.5° C./0.7 mmHg

Step iii) Production of 5-dodecylthiophene-2-carbaldehyde

In a 1 liter-four-necked flask, 93.7 g (1.28 mol) of N,N-dimethylformamide was placed and cooled to 5° C., followed by addition of 107.4 g ($7.00 \times 10^{-1}$ mol) of $POCl_3$ in 15 min. below 10° C. under stirring. After stirring for 30 min. below 10° C., 160 g ($6.35 \times 10^{-1}$ mol) of 2-dodecylthiophene was added dropwise to the mixture in 10 min. at room temperature, followed by stirring for 1.5 hours and further stirring for 2.5 hours at 60° C. After the reaction, the reaction mixture was poured into 2 liter of iced water, subjected to 3 times of extraction with 500 ml of chloroform and washed 6 times with 500 ml of water. The organic layer was dried on $CaCl_2$, followed by distilling-off of the solvent to obtain 237 g of a crude product. The crude product was subjected to reduced-pressure distillation in an atmosphere of nitrogen to obtain 135 g of a product (yield: 75.9%). b.p.: 160° C./0.6 mmHg

Step iv) Production of 5-dodecylthiophene-2-carboxylic acid

In a 2 liter-four-necked flask, 30.0 g ($1.07 \times 10^{-1}$ mol) of 5-dodecylthiophene-2-carbaldehyde, 6.0 g of NaOH, 21.3 g of $KMnO_4$ and 900 ml of water were placed and stirred for 17 hours at room temperature. After the reaction, the reaction mixture was acidified with conc. hydrochloric acid, followed by four times of extraction with 300 ml of ethyl acetate, three times of washing with 500 ml of water, drying with anhydrous magnesium sulfate and distilling-off of the solvent to obtain 29.9 g of a crude product. The crude product was purified by silica gel column chromatography with the use of an hexane/ethyl acetate (=2/1) mixture solvent and recrystallized from ethyl acetate to obtain 12.1 g of a pure product (yield: 38.2%).

Step v) Production of 2,3-dicyanohydroquinone monooctyl ether 16.2 g (57.1 mM) of n-octyl p-toluenesulfonate was added to the mixture of 6.5 g (40.8 mM) of dicyanohydroquinone and 50 ml of 5% NaOH aqueous solution, followed by 7 hours of stirring under refluxing. After the reaction, the reaction mixture was washed with toluene and the aqueous layer was acidified with HCl. The resultant precipitate was recovered through filtration and dried. To the precipitate, 1 liter of toluene was added. After the insoluble substrate was filtered out, the filtrate was subjected to recrystallization in a refrigerator and further subjected to recrystallization from a mixture solvent of water/methanol to obtain 3.4 g of an objective product (yield: 30.6%).

Step vi) Production of 2,3-dicyano-4-octyloxyphenyl 5-dodecylthiophene-2-carboxylate 0.50 g (1.69 mM) of 5-dodecylthiophene-2-carboxylic acid (M.W.: 296), 0.46 g (1.69 mM) of 2,3-dicyanohydroquinone monooctyl ether (M.W.: 272) and 20 ml of THF were mixed and stirred. To the mixture, 0.35 g (1.69 mM) of dicyclohexylcarbodiimide (M.W.: 206) and 0.05 g of pyrrolidinopyridine were added, followed by stirring overnight at room temperature. After the reaction, the reaction mixture was subjected to filtration and the filtrate was subjected to distillation to obtain a crude product. The crude product was purified by silica gel column chromatography with the use of benzene and recrystallized from ethanol to obtain 0.54 g of an objective product (yield: 58.1%).

Phase transition temperature (°C.)

$$\text{Cryst.} \xrightarrow[72.0]{78.7} \text{Iso.}$$

EXAMPLE 3

A liquid crystal composition A was prepared by mixing the following example compounds in respectively indicated proportions.

| Ex. Comp. No. | Structural formula | wt. parts |
|---|---|---|
| 8 | $C_8H_{17}O-\bigcirc-OC(=O)-\bigcirc-CH_2\overset{*}{C}H(CH_3)C_2H_5$ | 16 |
| 9 | $C_8H_{17}O-\bigcirc-CS(=O)-\bigcirc-CH_2\overset{*}{C}H(CH_3)C_2H_5$ | 22.5 |
| 18 | $C_8H_{17}O-\bigcirc-CO(=O)-\bigcirc-OCH_2\overset{*}{C}H(CH_3)C_2H_5$ | 64 |
| 23 | $C_8H_{17}-\bigcirc(N,N)-\bigcirc-O(CH_2)_5\overset{*}{C}H(CH_3)C_2H_5$ | 10 |

-continued

| Ex. Comp. No. | Structural formula | wt. parts |
|---|---|---|
| 24 | $C_{11}H_{23}O-\underset{N}{\overset{N}{\bigcirc}}-\bigcirc-O(CH_2)_2\overset{*}{C}H(CH_3)C_2H_5$ | 10 |
| 43 | $C_{10}H_{21}O-\bigcirc-\underset{O}{\overset{S}{C}}-\bigcirc-OCH_2\overset{*}{C}H(CH_3)C_2H_5$ | 22.5 |
| 63 | $C_{10}H_{21}O\underset{O}{\overset{\parallel}{C}}-\bigcirc-\bigcirc-O\underset{O}{\overset{\parallel}{C}}-\bigcirc-OCH_2\overset{*}{C}H(CH_3)OC_5H_{11}$ | 15 |
| 87 | $C_6H_{13}O\underset{O}{\overset{\parallel}{C}}-\bigcirc-\bigcirc-O\underset{O}{\overset{\parallel}{C}}-\bigcirc-OCH_2\overset{*}{C}H(CH_3)OC_8H_{17}$ | 15 |
| 124 | $C_{12}H_{25}O-\bigcirc-\underset{O}{\overset{\parallel}{C}}O-\bigcirc-OCH_2\overset{*}{C}H(F)C_6H_{13}$ | 6.75 |
| 136 | $C_8H_{17}O-\bigcirc-\underset{O}{\overset{\parallel}{C}}O-\bigcirc-OCH_2\overset{*}{C}H(F)C_5H_{11}$ | 18.75 |
| 236 | $C_3H_7-\bigcirc H-\underset{O}{\overset{\parallel}{C}}O-\bigcirc-\underset{N}{\overset{N}{\bigcirc}}-C_{12}H_{25}$ | 20 |

The liquid crystal composition A was further mixed with the following example compounds in the respectively proportions indicated below to provide a liquid crystal composition B.

| Ex. Comp. No. | Structural formula | wt. parts |
|---|---|---|
| 1-1 | $C_6H_{13}-\underset{S}{\bigcirc}-\underset{O}{\overset{\parallel}{C}}O-\bigcirc(CN)(CN)-OC_6H_{13}$ | 3 |
| 1-6 | $C_2H_5\overset{*}{C}H(CH_3)CH_2-\underset{S}{\bigcirc}-\underset{O}{\overset{\parallel}{C}}O-\bigcirc(CN)(CN)-OC_7H_{15}$ | 2 |
| | Composition A | 95 |

Two 0.7 mm-thick glass plates were provided and respectively coated with an ITO film to form an electrode for voltage application, which was further coated with an insulating layer of vapor-deposited SiO$_2$. On the insulating layer, a 0.2%-solution of silane coupling agent (KBM-602, available from Shinetsu Kagaku K.K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 Å-thick film The coating film was rubbed with acetate fiber-planted cloth. The thus treated two glass plates were washed with isopropyl alcohol. After alumina beads with an average particle size of 2.0 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell. The cell gap was found to be about 2 microns as measured by a Berek compensator.

Then, the liquid crystal composition B was heated into an isotropic liquid, and injected into the above prepared cell under vacuum and, after sealing, was gradually cooled at a rate of 20° C./hour to 25° C. to prepare a ferroelectric liquid crystal device.

The ferroelectric liquid crystal device was subjected to measurement of an optical response time (time from voltage application until the transmittance change reaches 90% of the maximum under the application of a peak-to-peak voltage Vpp of 20 V in combination with right-angle cross-nicol polarizers) and observation of switching states, etc.

In the ferroelectric liquid crystal device, a monodomain with a good and uniform alignment characteristic was observed.

The results are shown below.

|  | 15° C. | 25° C. | 35° C. |
|---|---|---|---|
| Response time (μsec) | 403 | 255 | 190 |

COMPARATIVE EXAMPLE 3

A ferroelectric liquid crystal device was prepared in the same manner as in Example 3 except that the liquid crystal composition A prepared in Example 3 was injected into a cell. The measured values of the response time of the device were as follows.

|  | 15° C. | 25° C. | 35° C. |
|---|---|---|---|
| Response time (μsec) | 450 | 270 | 195 |

EXAMPLE 4

A liquid crystal composition C was prepared in the same manner as in Example 3 except that the following example compounds were used in the indicated proportions instead of Example Compounds Nos. 1-1 and 1-6.

| Ex. Comp. No. | Structural formula | wt. parts |
|---|---|---|
| 1-4 | $C_{12}H_{25}$—[thiophene]—CO—[benzene with CN, CN]—$OC_8H_{17}$ (CO with =O) | 3 |
| 1-30 | $C_6H_{13}O$—[thiophene]—$CH_2O$—[benzene with CN, CN]—$OC_8H_{17}$ | 3 |
| 1-11 | $C_{12}H_{25}O$—[thiophene]—CO—[benzene with CN, CN]—$O(CH_2)_3CHOCH_3$ (with $CH_3$ branch) | 2 |
| Composition A |  | 92 |

A ferroelectric liquid crystal device was prepared in the same manner as in Example 3 except for using the liquid crystal composition C. In the ferroelectric liquid crystal device, a monodomain with a good and uniform alignment characteristic was observed. The ferroelectric liquid crystal device was subjected to measurement of response time in the same manner as in Example 3, whereby the following results were obtained.

|  | 15° C. | 25° C. | 35° C. |
|---|---|---|---|
| Response time (μsec) | 399 | 251 | 189 |

Further, when the device was driven, a clear switching action was observed, and good bistability was shown after the termination of the voltage application.

EXAMPLE 5

A liquid crystal composition D was prepared in the same manner as in Example 4 except that the following example compounds were used in the indicated proportions instead of Example Compounds Nos 1-4, 1-30 and 1-11.

| Ex. Comp. No. | Structural formula | wt. parts |
|---|---|---|
| 1-8 | $C_6H_{13}\overset{*}{C}H(F)CH_2$—[thiophene]—CO—[benzene with CN, CN]—$OC_{10}H_{21}$ | 2 |

| Ex. Comp. No. | Structural formula | wt. parts |
|---|---|---|
| 1-36 | $C_2H_5\overset{CH_3}{\underset{*}{C}H}(CH_2)_5\text{—[S]—}CH_2O\text{—[Ar(CN)(CN)]—}OCOC_{11}H_{23}$ | 2 |
| 1-18 | $C_6H_{13}O\text{—[S]—}CO\text{—[Ar(CN)(CN)]—}OCC_8H_{17}$ | 3 |
| Composition A | | 93 |

A ferroelectric liquid crystal device was prepared in the same manner as in Example 3 except for using the liquid crystal composition D. In the ferroelectric liquid crystal device, a monodomain with a good and uniform alignment characteristic was observed. The ferroelectric liquid crystal device was subjected to measurement of response time in the same manner as in Example 3, whereby the following results were obtained.

| | 15° C. | 25° C. | 35° C. |
|---|---|---|---|
| Response time (μsec) | 364 | 220 | 165 |

Further, when the device was driven, a clear switching action was observed, and good bistability was shown after the termination of the voltage application

EXAMPLE 6

A liquid crystal composition E was prepared in the same manner as in Example 5 except that the following example compounds were used in the indicated proportions instead of Example Compounds Nos. 1-8, 1-36 and 1-18.

| Ex. Comp. No. | Structural formula | wt. parts |
|---|---|---|
| 1-12 | $C_8H_{17}C(=O)\text{—[S]—}CO\text{—[Ar(CN)(CN)]—}OCH_2\overset{F}{\underset{*}{C}H}C_6H_{13}$ | 2 |
| 1-13 | $C_9H_{19}OCO\text{—[S]—}CO\text{—[Ar(CN)(CN)]—}OC_7H_{15}$ | 3 |
| 1-29 | $C_6H_{13}\text{—[S]—}CH_2O\text{—[Ar(CN)(CN)]—}OC_6H_{13}$ | 3 |
| Composition A | | 92 |

A ferroelectric liquid crystal device was prepared in the same manner as in Example 3 except for using the liquid crystal composition E. In the ferroelectric liquid crystal device, a monodomain with a good and uniform alignment characteristic was observed. The ferroelectric liquid crystal device was subjected to measurement of response time in the same manner as in Example 3, whereby the following results were obtained.

| | 15° C. | 25° C. | 35° C. |
|---|---|---|---|
| Response time (μsec) | 372 | 230 | 172 |

Further, when the device was driven, a clear switching action was observed, and good bistability was shown after the termination of the voltage application

EXAMPLE 7

A commercially available ferroelectric liquid crystal ("CS-1014" available from Chisso K.K.) having a Δε of nearly 0 (Δε≃−0.4 (sine wave, 100 kHz)) and the following example compound were mixed in the indicated proportions to prepare a liquid crystal composition F

| Ex. Comp. No. | Structural formula | wt. parts |
|---|---|---|
| 1-1 | 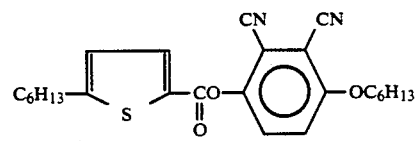 | 6 |

| Ex. Comp. No. | Structural formula | wt. parts |
| --- | --- | --- |
| 1-4 | C$_{12}$H$_{25}$—[thiophene]—CO—[benzene(CN)(CN)]—OC$_8$H$_{17}$ | 4 |
| 1-17 | C$_{11}$H$_{23}$CO—[thiophene]—CO—[benzene(CN)(CN)]—OCH$_2$*CH(CH$_3$)C$_2$H$_5$ | 2 |
| CS-1014 | | 94 |

| | Structural formula | wt. parts |
| --- | --- | --- |
| Ex. Comp. No. | | |
| CS-1014 | | 94 |

Ferroelectric liquid crystal devices were prepared in the same manner as in Example 3 except that the above liquid crystal CS1014 and the liquid crystal composition F were used respectively and the liquid crystal layer thicknesses were changed to 1.5 microns.

The above liquid crystal devices were subjected to measurement of a tilt angle under right angle cross nicols at 25° C. Then, the devices were subjected application of a ±8 V rectangular waveform at a frequency of 60 kHz, and the tilt angles were measured under the voltage application and microscopic observation. Under these conditions, the transmittances and contrast ratios were measured. The results are shown below.

| | CS-1014 | Composition F |
| --- | --- | --- |
| Tilt angle (under right angle cross nicols) | 7 degrees | 7.2 degrees |
| Tilt angle (under application ±8 V, 60 KHz) | 8.8 degrees | 12.8 degrees |
| Transmittance (under application ±8 V, 60 KHz) | 7.8% | 14.2% |
| Contrast ratio (under application ±8 V, 60 KHz) | 8:1 | 57:1 |

The above results show the addition of the mesomorphic compound example of the present invention to a liquid crystal CS 1014 having a Δε of nearly 0 provided a liquid crystal device showing improved display characteristics due to AC stabilization effect.

EXAMPLE 8

A liquid crystal composition G was prepared in the same manner as in Example 7 except that the following example compounds were used in the indicated proportions instead of Example Compound No. 1-1.

Ferroelectric liquid crystal devices were prepared in the same manner as in Example 3 except that the above liquid crystal CS1014 and the liquid crystal composition G were used respectively and the liquid crystal layer thicknesses were changed to 1.5 microns.

The above liquid crystal devices were subjected to measurement of a tilt angle under right angle cross nicols at 25° C. Then, the devices were subjected application of a ±8 V rectangular waveform at a frequency of 60 kHz, and the tilt angles were measured under the voltage application and microscopic observation. Under these conditions, the transmittances and contrast ratios were measured. The results are shown below.

| | CS-1014 | Composition G |
| --- | --- | --- |
| Tilt angle (under right angle cross nicols) | 7 degrees | 7.1 degrees |
| Tilt angle (under application ±8 V, 60 KHz) | 8.8 degrees | 12.3 degrees |
| Transmittance (under application ±8 V, 60 KHz) | 7.8% | 12.9% |
| Contrast ratio (under application ±8 V, 60 KHz) | 8:1 | 55:1 |

The above results show the addition of the mesomorphic compound example of the present invention to a liquid crystal CS 1014 having a Δε of nearly 0 provided a liquid crystal device showing improved display characteristics due to AC stabilization effect.

EXAMPLE 9

A liquid crystal composition H was prepared in the same manner as in Example 8 except that the following example compounds were used in the indicated proportions instead of Example Compounds Nos. 1-4 and 1-7.

| Ex. Comp. No. | Structural formula | wt. parts |
| --- | --- | --- |
| 1-2 | C$_8$H$_{17}$O—[thiophene]—CO—[benzene(CN)(CN)]—OC$_{10}$H$_{21}$ | 3 |

| Ex. Comp. No. | Structural formula | wt. parts |
|---|---|---|
| 1-31 | C$_8$H$_{17}$C(=O)-[S ring]-CH$_2$O-[benzene with CN, CN]-OCC$_8$H$_{17}$(=O) | 2 |
| 1-33 | C$_{10}$H$_{21}$OC(=O)-[S ring]-CH$_2$O-[benzene with CN, CN]-OCC$_{11}$H$_{23}$(=O) | 2 |
| CS-1014 | | 93 |

Ferroelectric liquid crystal devices were prepared in the same manner as in Example 3 except that the above liquid crystal CS1014 and the liquid crystal composition H were used respectively and the liquid crystal layer thicknesses were changed to 1.5 microns.

The above liquid crystal devices were subjected to measurement of a tilt angle under right angle cross nicols at 25° C. Then, the devices were subjected application of a ±8 V rectangular waveform at a frequency of 60 kHz, and the tilt angles were measured under the voltage application and microscopic observation. Under these conditions, the transmittances and contrast ratios were measured. The results are shown below.

|  | CS-1014 | Composition H |
|---|---|---|
| Tilt angle (under right angle cross nicols) | 7 degrees | 7.5 degrees |

-continued

|  | CS-1014 | Composition H |
|---|---|---|
| Tilt angle (under application ±8 V, 60 KHz) | 8.8 degrees | 13.6 degrees |
| Transmittance (under application ±8 V, 60 KHz) | 7.8% | 15.5% |
| Contrast ratio (under application ±8 V, 60 KHz) | 8:1 | 63:1 |

The above results show the addition of the mesomorphic compound example of the present invention to a liquid crystal CS 1014 having a Δε of nearly 0 provided a liquid crystal device showing improved display characteristics due to AC stabilization effect.

EXAMPLE 10

A liquid crystal composition I was prepared by mixing the following example compounds in respectively indicated proportions.

| Ex. Comp. No. | Structural formula | wt. parts |
|---|---|---|
| 9 | C$_8$H$_{17}$O-[benzene]-COS-[benzene]-CH$_2$C*HC$_2$H$_5$ (with CH$_3$) | 18 |
| 245 | C$_{12}$H$_{25}$O-[benzene]-COS-[benzene]-CH$_2$C*HC$_2$H$_5$ (with CH$_3$) | 18 |
| 246 | C$_8$H$_{17}$O-[benzene]-COS-[benzene]-OCH$_2$C*HC$_2$H$_5$ (with CH$_3$) | 8 |
| 43 | C$_{10}$H$_{21}$O-[benzene]-COS-[benzene]-OCH$_2$C*HC$_2$PH$_5$ (with CH$_3$) | 8 |
| 87 | C$_8$H$_{17}$OC*HCH$_2$O-[benzene]-COO-[benzene]-[benzene]-COOC$_6$H$_{13}$ (with CH$_3$) | 12 |
| 247 | C$_4$H$_9$OCH$_2$CH$_2$O-[benzene]-COO-[benzene]-[benzene]-COOC$_6$H$_{13}$ | 12 |

-continued

| Ex. Comp. No. | Structural formula | wt. parts |
|---|---|---|
| 63 | $C_5H_{11}O\overset{*}{C}H(CH_3)CH_2O$—⟨phenyl⟩—COO—⟨phenyl⟩—⟨phenyl⟩—$COOC_{10}H_{21}$ | 6 |
| 171 | $C_6H_{13}$—⟨pyrimidine(N,N)⟩—⟨phenyl⟩—$OC_8H_{17}$ | 6 |
| 248 | $C_8H_{17}$—⟨pyrimidine(N,N)⟩—⟨phenyl⟩—$OC_{10}H_{21}$ | 6 |
| 191 | $C_5H_{11}$—⟨pyrimidine(N,N)⟩—⟨phenyl⟩—⟨phenyl⟩—$C_6H_{13}$ | 4 |
| 249 | $C_9H_{19}$—⟨phenyl⟩—⟨phenyl⟩—⟨pyrimidine(N,N)⟩—$C_7H_{15}$ | 2 |

The liquid crystal composition I was further mixed with the following example compounds in the respectively proportions indicated below to provide a liquid crystal composition J.

| Ex. Comp. No. | Structural formula | wt. parts |
|---|---|---|
| 1-4 | $C_{12}H_{25}$—⟨thiophene⟩—CO—O—⟨phenyl(CN,CN)⟩—$OC_8H_{17}$ | 3 |
| 1-20 | $C_{11}H_{23}O$—⟨thiophene⟩—CO—O—⟨phenyl(CN,CN)⟩—$OC_8H_{17}$ | 3 |
| Composition I | | 94 |

A ferroelectric liquid crystal device was prepared in the same manner as in Example 3 except for using the composition J. In the ferroelectric liquid crystal device, a monodomain with a good and uniform alignment characteristic was observed. The ferroelectric liquid crystal device was subjected to measurement of response time and observation of a switching state, etc. in the same manner as in Example 3, whereby the following results were obtained.

|  | 15° C. | 25° C. | 35° C. |
|---|---|---|---|
| Response time (μsec) | 1080 | 470 | 231 |

COMPARATIVE EXAMPLE 10

A ferroelectric liquid crystal device was prepared in the same manner as in Example 3 except that the liquid crystal composition I prepared in Example 10 was injected into a cell. The measured values of the response time of the device were as follows.

|  | 15° C. | 25° C. | 35° C. |
|---|---|---|---|
| Response time (μsec) | 1260 | 535 | 245 |

EXAMPLE 11

A liquid crystal composition K was prepared in the same manner as in Example 10 except that the following example compounds were used in the indicated proportions instead of Example Compounds Nos. 1-4 and 1-20.

| Ex. Comp. No. | Structural formula | wt. parts |
|---|---|---|
| 1-14 | $C_{12}H_{25}$—[thiophene]—CO—O—[benzene with CN, CN]—$OC_6H_{13}$ | 3 |
| 1-18 | $C_6H_{13}O$—[thiophene]—CO—O—[benzene with CN, CN]—$OCC_8H_{17}$ (with C=O) | 2 |
| 1-42 | $C_8H_{17}C(=O)$—[thiophene]—$CH_2O$—[benzene with CN, CN]—$O\text{-}(CH_2)_2\text{-}CHOCH_3$ (with $CH_3$ branch) | 2 |
| | Composition I | 93 |

A ferroelectric liquid crystal device was prepared in the same manner as in Example 3 except for using the liquid crystal composition K. In the ferroelectric liquid crystal device, a monodomain with a good and uniform alignment characteristic was observed. The ferroelectric liquid crystal device was subjected to measurement of response time in the same manner as in Example 3, whereby the following results were obtained.

| | 15° C. | 25° C. | 35° C. |
|---|---|---|---|
| Response time (μsec) | 1105 | 482 | 236 |

Further, when the device was driven, a clear switching action was observed, and good bistability was shown after the termination of the voltage application.

EXAMPLE 12

A liquid crystal composition L was prepared in the same manner as in Example 10 except that the following example compounds were used in the indicated proportions instead of Example Compounds Nos. 1-4 and 1-20.

| Ex. Comp. No. | Structural formula | wt. parts |
|---|---|---|
| 1-5 | $C_7H_{15}CO(=O)$—[thiophene]—CO—O—[benzene with CN, CN]—$OC_9H_{19}$ | 2 |
| 1-19 | $C_{11}H_{23}$—[thiophene]—CO—O—[benzene with CN, CN]—$OC_8H_{17}$ | 3 |
| | Composition I | 95 |

A ferroelectric liquid crystal device was prepared in the same manner as in Example 3 except for using the liquid crystal composition L. In the ferroelectric liquid crystal device, a monodomain with a good and uniform alignment characteristic was observed. The ferroelectric liquid crystal device was subjected to measurement of response time in the same manner as in Example 3, whereby the following results were obtained.

| | 15° C. | 25° C. | 35° C. |
|---|---|---|---|
| Response time (μsec) | 1135 | 492 | 241 |

Further, when the device was driven, a clear switching action was observed, and good bistability was shown after the termination of the voltage application.

As is understood from the results of the above examples, the liquid crystal composition and the liquid crystal device according to the present invention using the mesomorphic compound represented by the formula (I) show good switching characteristic, good responsiveness and remarkably improved display characteristic when applied to a display method utilizing the AC stabilization effect.

What is claimed is:

1. A mesomorphic compound represented by the following formula (I):

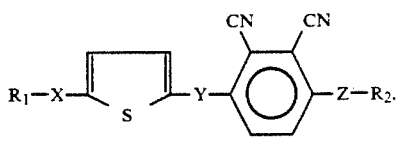 (1)

wherein $R_1$ and $R_2$ denote a linear or branched alkyl group having 1-18 carbon atoms which are unsubstituted or substituted by fluorine or alkoxy group; X denotes any one of a single bond, —O—,

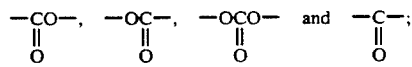

Y denotes

—CO—
  ‖
  O or —CH$_2$O—; and Z denotes any one of —O—,

—OC— and —OCO—.
 ‖           ‖
 O           O

2. A mesomorphic compound according to claim 1, wherein X is any one of a single bond, —O—, and

and $R_1$ and $R_2$ are respectively any one of groups (i) to (iv) shown below:
(i) n-alkyl group having 1-18 carbon atoms;
(ii)

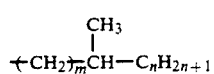

wherein m is 1-7 and n is 2-9 (optically active or inactive);
(iii)

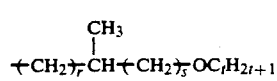

wherein r is 0-7, s is 0 or 1 and t is 1-14 (optically active or inactive); and
(iv)

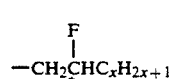

wherein x is 1-16.

3. A mesomorphic compound according to claim 1, which is represented by the following formula:

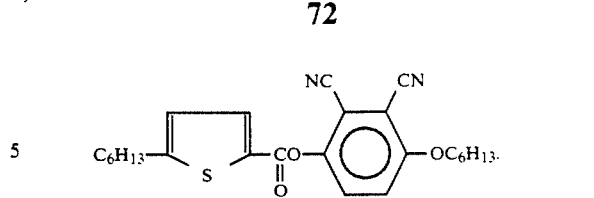

4. A mesomorphic compound according to claim 1, which is represented by the following formula:

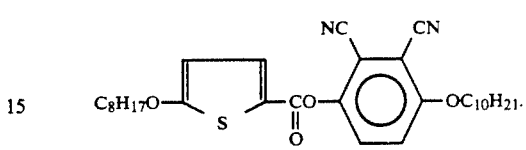

5. A mesomorphic compound according to claim 1, which is represented by the following formula:

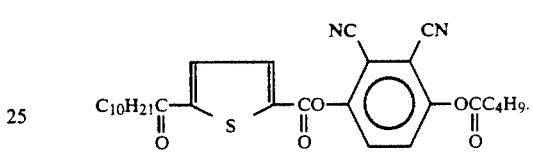

6. A mesomorphic compound according to claim 1, which is represented by the following formula:

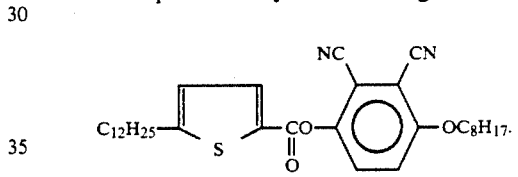

7. A mesomorphic compound according to claim 1, which is represented by the following formula:

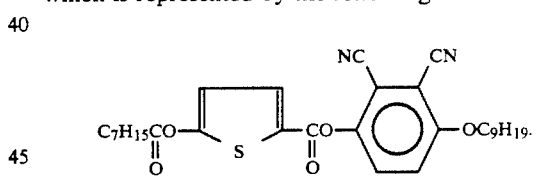

8. A mesomorphic compound according to claim 1, which is represented by the following formula:

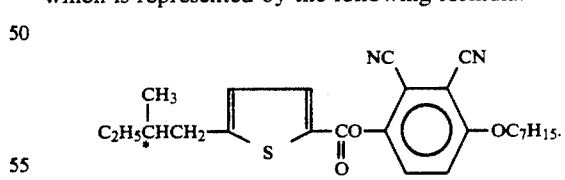

9. A mesomorphic compound according to claim 1, which is represented by the following formula:

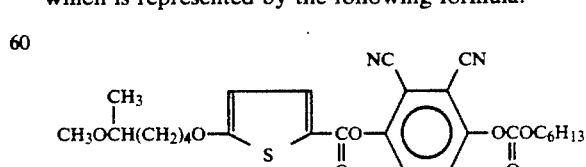

10. A mesomorphic compound according to claim 1, which is represented by the following formula:

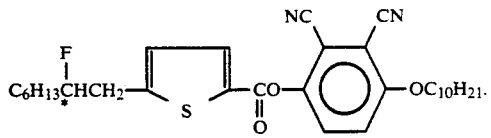

11. A mesomorphic compound according to claim 1, which is represented by the following formula:

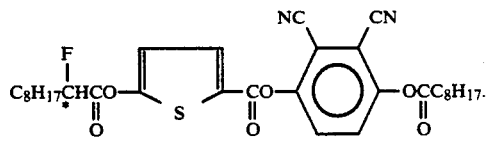

12. A mesomorphic compound according to claim 1, which is represented by the following formula:

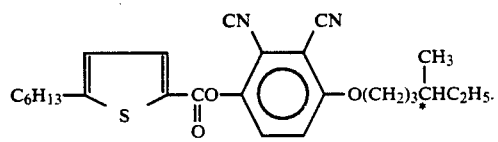

13. A mesomorphic compound according to claim 1, which is represented by the following formula:

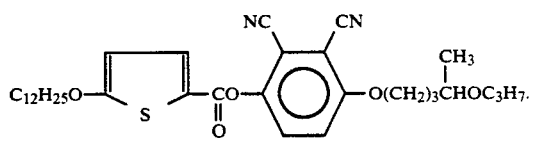

14. A mesomorphic compound according to claim 1, which is represented by the following formula:

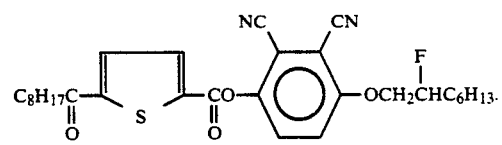

15. A mesomorphic compound according to claim 1, which is represented by the following formula:

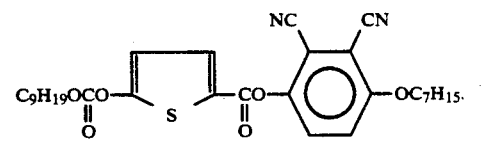

16. A mesomorphic compound according to claim 1, which is represented by the following formula:

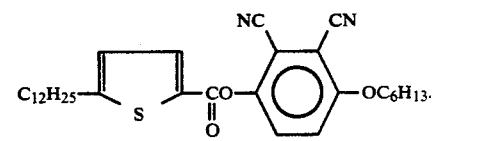

17. A mesomorphic compound according to claim 1, which is represented by the following formula:

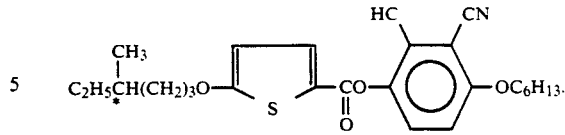

18. A mesomorphic compound according to claim 1, which is represented by the following formula:

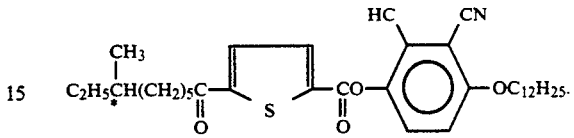

19. A mesomorphic compound according to claim 1, which is represented by the following formula:

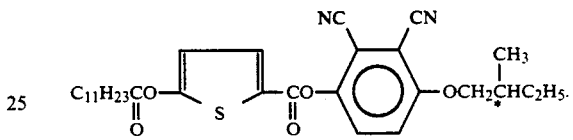

20. A mesomorphic compound according to claim 1, which is represented by the following formula:

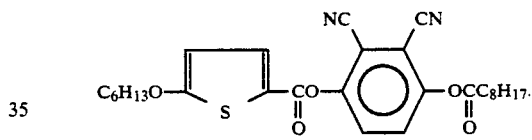

21. A mesomorphic compound according to claim 1, which is represented by the following formula:

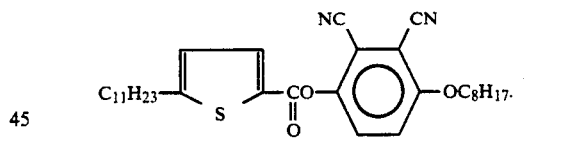

22. A mesomorphic compound according to claim 1, which is represented by the following formula:

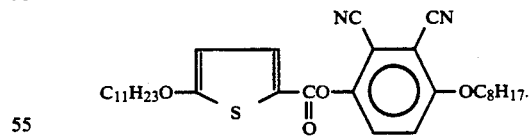

23. A mesomorphic compound according to claim 1, which is represented by the following formula:

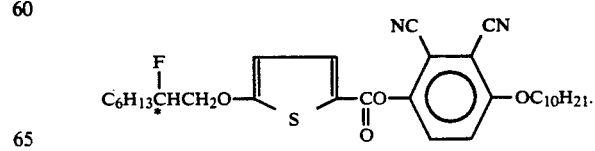

24. A mesomorphic compound according to claim 1, which is represented by the following formula:

25. A mesomorphic compound according to claim 1, which is represented by the following formula:

C6H13*CHF-CH2O-[thiophene]-CO-O-[benzene(NC)(CN)]-OCC8H17
                                                        ||
                                                        O

26. A mesomorphic compound according to claim 1, which is represented by the following formula:

C5H11*CHF-CH2-[thiophene]-CO-O-[benzene(NC)(CN)]-OC11H23
                           ||
                           O

27. A mesomorphic compound according to claim 1, which is represented by the following formula:

C2H5*CH(CH3)-CH2O-[thiophene]-CO-O-[benzene(NC)(CN)]-OCH2*CH(CH3)C2H5
                               ||
                               O

28. A mesomorphic compound according to claim 1, which is represented by the following formula:

C2H5*CH(CH3)(CH2)3-[thiophene]-CO-O-[benzene(NC)(CN)]-OCC6H13
                                ||                     ||
                                O                      O

29. A mesomorphic compound according to claim 1, which is represented by the following formula:

C2H5*CH(CH3)(CH2)3O-[thiophene]-CO-O-[benzene(NC)(CN)]-OCC12H25
                                 ||                     ||
                                 O                      O

30. A mesomorphic compound according to claim 1, which is represented by the following formula:

C3H7OCH(CH3)(CH2)3OC-[thiophene]-CO-O-[benzene(NC)(CN)]-OC9H19
                  ||              ||
                  O               O

31. A mesomorphic compound according to claim 1, which is represented by the following formula:

CH3OCH(CH3)(CH2)4-[thiophene]-CO-O-[benzene(NC)(CN)]-OCOC6H13
                               ||
                               O

32. A mesomorphic compound according to claim 1, which is represented by the following formula:

C6H13-[thiophene]-CH2O-[benzene(NC)(CN)]-OC6H13

33. A mesomorphic compound according to claim 1, which is represented by the following formula:

C6H13O-[thiophene]-CH2O-[benzene(NC)(CN)]-OC8H17

34. A mesomorphic compound according to claim 1, which is represented by the following formula:

C8H17C-[thiophene]-CH2O-[benzene(NC)(CN)]-OCC8H17
     ||                                     ||
     O                                      O

35. A mesomorphic compound according to claim 1, which is represented by the following formula:

C10H21CO-[thiophene]-CH2O-[benzene(NC)(CN)]-OCC6H13
      ||                                     ||
      O                                      O

36. A mesomorphic compound according to claim 1, which is represented by the following formula:

C10H21OC-[thiophene]-CH2O-[benzene(NC)(CN)]-CCC11H23
       ||                                    ||
       O                                     O

37. A mesomorphic compound according to claim 1, which is represented by the following formula:

C2H5*CH(CH3)CH2-[thiophene]-CH2O-[benzene(NC)(CN)]-OCC9H19
                                                    ||
                                                    O

38. A mesomorphic compound according to claim 1, which is represented by the following formula:

C2H5*CH(CH3)CH2O-[thiophene]-CH2O-[benzene(NC)(CN)]-OC12H25

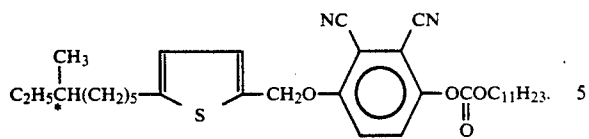

39. A mesomorphic compound according to claim 1, which is represented by the following formula:

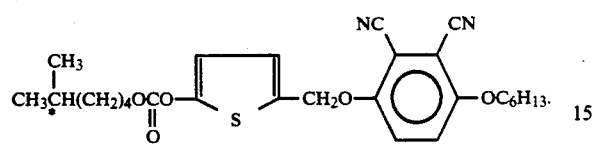

40. A mesomorphic compound according to claim 1, which is represented by the following formula:

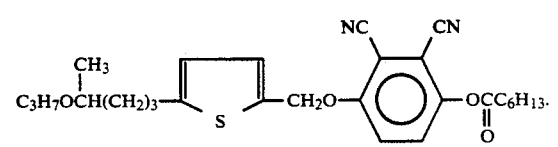

41. A mesomorphic compound according to claim 1, which is represented by the following formula:

42. A mesomorphic compound according to claim 1, which is represented by the following formula:

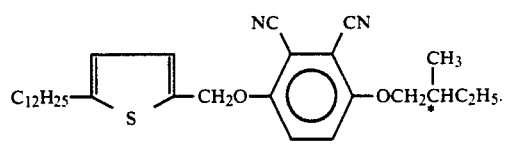

43. A mesomorphic compound according to claim 1, which is represented by the following formula:

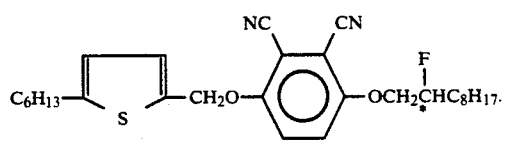

44. A mesomorphic compound according to claim 1, which is represented by the following formula:

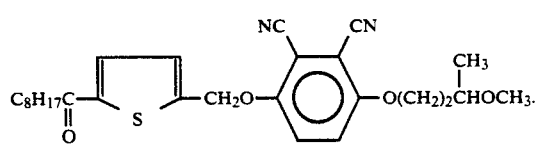

45. A mesomorphic compound according to claim 1, which is represented by the following formula

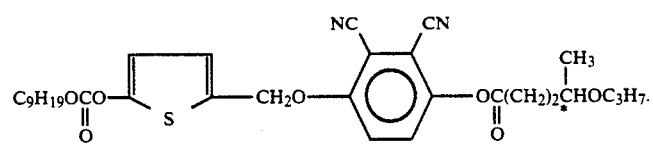

46. A liquid crystal composition comprising at least two mesomorphic compounds, at least one which is a mesomorphic compound according to claim 1.

47. A liquid crystal device, comprising a pair of electrode plates and a liquid crystal composition according to claim 46 disposed between the electrode plates.

* * * * *

UNITED STATES PATENT AND TRADEMARK OFFICE
CERTIFICATE OF CORRECTION

PATENT NO. : 5,118,441
DATED : June 2, 1992
INVENTOR(S) : SHOSEI MORI, ET AL.

It is certified that error appears in the above-identified patent and that said Letters Patent is hereby corrected as shown below:

COLUMN 1

Line 37, "discriminateable" should read --discriminatable--.
Line 56, "(µ)" should read --($\vec{\mu}$)--.

COLUMN 50

Line 62, "steps i(-vi)." should read --steps i) - vi).--.

COLUMN 57

Line 41, "tively" should read --tive--.

COLUMN 58

Line 63, "film" should read --film.--.

COLUMN 61

Line 33, "application" should read --application.--.

COLUMN 62

Line 27, "application" should read --application.--.
Line 34, "F" should read --F.--.

COLUMN 63

Line 33, "subjected" should read --subjected to--.

UNITED STATES PATENT AND TRADEMARK OFFICE
CERTIFICATE OF CORRECTION

PATENT NO. : 5,118,441
DATED : June 2, 1992
INVENTOR(S) : SHOSEI MORI, ET AL.

Page 2 of 2

It is certified that error appears in the above-identified patent and that said Letters Patent is hereby corrected as shown below:

<u>COLUMN 78</u>

```
Line 30, "formula" should read --formula:--.
Line 39, "one" should read --one of--.
```

Signed and Sealed this

Twelfth Day of October, 1993

*Attest:*

BRUCE LEHMAN

*Attesting Officer*   *Commissioner of Patents and Trademarks*